US009243290B2

(12) United States Patent
Edwards

(10) Patent No.: US 9,243,290 B2

(45) Date of Patent: Jan. 26, 2016

(54) POLONY SEQUENCING METHODS

(75) Inventor: Jeremy Edwards, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 2 days.

(21) Appl. No.: 13/500,578

(22) PCT Filed: Oct. 8, 2010

(86) PCT No.: PCT/US2010/051938

§ 371 (c)(1), (2), (4) Date: Jun. 8, 2012

(87) PCT Pub. No.: WO2011/044437

PCT Pub. Date: Apr. 14, 2011

(65) Prior Publication Data

US 2012/0270740 A1 Oct. 25, 2012

Related U.S. Application Data

(60) Provisional application No. 61/250,209, filed on Oct. 9, 2009, provisional application No. 61/264,909, filed on Nov. 30, 2009, provisional application No. 61/313,365, filed on Mar. 12, 2010.

(51) Int. Cl.
*C12Q 1/68* (2006.01)

(52) U.S. Cl.
CPC ............ *C12Q 1/6874* (2013.01); *C12Q 1/6869* (2013.01)

(58) Field of Classification Search
USPC .......................................... 435/6.1; 506/9, 26
See application file for complete search history.

(56) References Cited

U.S. PATENT DOCUMENTS

| | | | | |
|---|---|---|---|---|
| 5,525,464 | A * | 6/1996 | Drmanac et al. | 435/6.18 |
| 6,274,320 | B1 | 8/2001 | Rothberg | |
| 2004/0126776 | A1 | 7/2004 | Hofer et al. | |
| 2004/0209298 | A1 | 10/2004 | Kamberov et al. | |
| 2006/0008824 | A1 | 1/2006 | Ronaghi et al. | |
| 2006/0040297 | A1 | 2/2006 | Leamon et al. | |
| 2008/0003571 | A1 * | 1/2008 | McKernan et al. | 435/6 |
| 2009/0176652 | A1 | 7/2009 | Dahl et al. | |
| 2011/0045992 | A1 * | 2/2011 | Shao et al. | 506/7 |

FOREIGN PATENT DOCUMENTS

| | | |
|---|---|---|
| WO | WO 2007/133740 | 11/2007 |
| WO | WO 2009065355 A1 * | 5/2009 |

OTHER PUBLICATIONS

International Search Report and Written Opinion issued by the Korean Intellectual Property Office for PCT/US2012/051938, on Sep. 8, 2011; 21 pgs.

International Preliminary Report on Patentability issued by the International Bureau of WIPO for PCT/US2012/051938, on Apr. 19, 2012; 11 pgs.

Bailey, J. A. et al., "Recent segmental duplications in the human genome," *Science*, Aug. 9, 2002;297:1003-1007.

Barany, F., "Genetic disease detection and DNA amplification using cloned thermostable ligase," *Proc Natl Acad Sci USA*, Jan. 1991;88(1):189-193.

Barany et al., "Cloning, overexpression and nucleotide sequence of a thermostable DNA ligase-encoding gene," *Gene*, Sep. 1991;109: 1-11.

Butz et al., "Detection of allelic variations of human gene expression by polymerase colonies," *BMC Genetics*, Feb. 16, 2004;5: 5 pgs.

Butz et al., "Characterization of Mutations and loss of heterozygosity of p53 and K-*ras*2 in Pancreatic Cancer Cell Lines by Immobilized polymerase chain reaction," *BMC Biotechnol*, Jul. 23, 2003;3:6 pgs.

Butz et al., "Detecting changes in the relative expression of KRAS2 splice variants using polymerase colonies," *Biotechnol Prog*, Oct. 23, 2004;20:1836-1839.

Carroll et al., "Droplet-Based Microfluidics for Emulsion and Solvent Evaporation Synthesis of Monodisperse Mesoporous Silica Microspheres," *Langmuir*, Jan. 3, 2008;24:658-661.

Collins et al., "The Human Genome Project: lessons from large-scale biology," *Science*, Apr. 11, 2003;300:286-290.

Cutler et al., "High-throughput variation detection and genotyping using microarrays," *Genome Res*, Aug. 23, 2001;11:1913-1925.

Diehl et al., "Detection and quantification of mutations in the plasma of patients with colorectal tumors," *Proc Natl Acad Sci USA*, Nov. 8, 2005;102(45):16368-16373.

Di Giusto et al., "Single base extension (SBE) with proofreading polymerases and phosphorothioate primers: improved fidelity in single-substrate assays," *Nucleic Acids Res*, Feb. 7, 2003;31:e7: 12 pgs.

Dressman et al., "Transforming single DNA molecules into fluorescent magnetic particles for detection and enumeration of genetic variations," *Proc Natl Acad Sci USA*, Jul. 22, 2003;100(15):8817-8822.

Eckstein et al., "Phosphorothioates in molecular biology," *Trends Biochem Sci*, Mar. 1989;14:97-100.

(Continued)

*Primary Examiner* — Samuel Woolwine
*Assistant Examiner* — Kaijiang Zhang
(74) *Attorney, Agent, or Firm* — Mueting Raasch & Gebhardt, P.A.

(57) ABSTRACT

We describe ultra-high throughput polony genome sequencing that can permit, for example, generating raw data to re-sequencing the human genome in about one week (including library prep and sequencing) at a reasonable cost. The methods described herein include one or more of the following: (1) increasing polony sequencing read length, (2) improving library construction and emulsions protocols, (3) increasing bead density and/or moving to alternative clonal amplication strategies (other than emulsion PCR or ePCR), (4) extending software capabilities to allow SNP calls from our new sequencing raw data, (5) Dual Primer Emulsion PCR, and (6) diagnostic method exploiting one or more of the foregoing.

3 Claims, 32 Drawing Sheets

(56) References Cited

OTHER PUBLICATIONS

Ewing et al., "Base-calling of automated sequencer traces using Phred. II. Error probabilities," *Genome Res*, Feb. 3, 1998; 8:186-194.
Ewing et al., "Base-calling of automated sequencer traces using Phred. I. Accuracy assessment," *Genome Res*, Feb. 3, 1998;8: 175-185.
Gish et al., "DNA and RNA sequence determination based on phosphorothioate chemistry," *Science*, Jun. 10, 1988;240: 1520-1522.
Housby et al., "*Thermus scotoductus* and *Rhodothermus marinus* DNA ligases have higher ligation efficiencies than *Thermus thermophilus* DNA ligase," *Anal Biochem*, Jan. 30, 2002;302:88-94.
Housby et al., "Optimised ligation of oligonucleotides by thermal ligases: comparison of *Thermus scotoductus* and *Rhodothermus marinus* DNA ligases to other thermophilic ligases," *Nucleic Acids Res*, 2000;28(3): E10: 5 pgs.
Joneitz, "Personal Genomes," Technology Review, Oct. 2001 [online] Retrieved from the Internet:<URL:http://staging.technologyreview.com/article/401208/personal-genomes/; 2 pgs.
Langmead et al., "Ultrafast and memory-efficient alignment of short DNA sequences to the human genome," *Genome Biol*, Mar. 4, 2009;10(3):R25: 10 pgs.
Larson et al., "MRE11/RAD50 Cleaves DNA in the AID/UNG-dependent pathway of immunoglobulin gene diversification," *Mol Cell*, Nov. 11, 2005; 20: 367-375.
Li, J. et al., "A colorimetric method for point mutation detection using high-fidelity DNA ligase," *Nucleic Acids Res*, Oct. 27, 2005; 33(19): e168: 9 pgs.
Link et al., "Electric Control of Droplets in Microfluidic Devices,", *Angew. Chem. Int. Ed.*, Mar. 17, 2006;45(16):2556-2560.
Liu et al., "DNA ligases ensure fidelity by interrogating minor groove contacts," *Nucleic Acids Res*, Aug. 24, 2004;32(15): 4503-4511.
Luo et al., "Improving the fidelity of *Thermus thermophilus* DNA ligase," *Nucleic Acids Res*, May 28, 1996;24(14): 3071-3078.
Luo et al., "Identification of essential residues in *Thermus thermophilus* DNA ligase," *Nucleic Acids Res*, May 28, 1996; 24(15):3079-3085.
Merritt et al., "Assaying gene function by growth competition experiment," *Metab Eng*, Jul. 2004; 6:212-219.
Merritt et al., "Parallel analysis of Mutant Human Glucose 6-Phosphate Dehyudrogenase in Yeast Using PCR Colonies," *Biotech Bioeng*, Dec. 5, 2005; 92(5):519-531.
Merritt et al., "Parallel competition analysis of *Saccharomyces cerevisiae* strains differing by a single base using polymerase colonies," *Nucleic Acids Res*, Jun. 3, 2003;31(15): e84: 8 pgs.
Mikkilineni et al., "Digital Quantitative Measurements of Gene Expression," *Biotech Bioeng*, Apr. 20, 2004; 86(2): 117-124.
Mitra et al., "In situ localized amplification and contact replication of many individual DNA molecules," *Nucleic Acids Res*, Oct. 1, 1999; 27(24): e34: 6 pgs.
Mitra et al., "Digital genotyping and haplotyping with polymerase colonies," *Proc Natl Acad Sci USA*, May 13, 2003;100(10):5926-5931.
Mitra et al., "Fluorescent in situ sequencing on polymerase colonies," *Anal Biochem*, Jan. 7, 2003;320: 55-65.
Nakamaye et al., "Direct sequencing of polymerase chain reaction amplified DNA fragments through the incorporation of deoxynucleoside alpha-thiotriphosphates," *Nucleic Acids Res*, Oct. 7, 1988;16(21):9947-9959.
Pennisi, "Gene Researchers Hunt Bargains, Fixer-Uppers," *Science*, Oct. 25, 2002; 298:735-736.
Pihlak et al., "Rapid genome sequencing with short universal tiling probes," *Nat Biotechnol*, Jun. 2008;26(6):676-684.
Pray, L., "A cheap personal genome," *The Scientist*, Oct. 4, 2002 [online]; Retrieved from the Internet:<URL: http://www.the-scientist.com/?articles.view/articleNo/21611/title/A-cheap-personal-genome-/>; 2 pgs.
Pritchard et al., "Effects of base mismatches on joining of short oligodeoxynucleotides by DNA ligases," *Nucleic Acids Res*, Jul. 15, 1997;25(17): 3403-3407.
Rodriguez et al., "High frequency of homozygosity of the HLA region in melanoma cell lines reveals a pattern compatible with extensive loss of heterozygosity," *Cancer Immunol Immunother*, Feb. 2005;54(2):141-148.
Schmitz et al., "Dropspots: a picoliter array in a microfluidic device," *Lab on a Chip*, Jan. 2009;9(1):44-49.
Shendure et al., "Accurate multiplex polony sequencing of an evolved bacterial genome," *Science*, Sep. 9, 2005;309(5741):1728-1732.
Shendure et al., "Advanced sequencing technologies: Methods and goals," *Nature Reviews Genetics*, May 2004; 5:335-345.
Sjoblom et al., "The consensus coding sequences of human breast and colorectal cancers," *Science*, Oct. 13, 2006; 314: 268-274.
Thiam et al., "Breaking of an Emulsion under an ac Electric Field," *Phys. Rev. Lett.*, May 8, 2009;102(18):188304-188307.
Tong et al., "Biochemical properties of a high fidelity DNA ligase from *Thermus* species AK16D," *Nucleic Acids Res*, Feb. 1999; 27(3):788-794.
Tong et al., "Ligation reaction specificities of an NAD(+)-dependent DNA ligase from the hyperthermophile *Aquifex aeolicus," Nucleic Acids Res*, Mar. 1999;28(6):1447-1454.
Wang et al., "Digital karyotyping identifies thymidylate synthase amplification as a mechanism of resistance to 5-fluorouracil in metastatic colorectal cancer patients," *Proc Natl Acad Sci U S A*, Mar. 2, 2004;101(9):3089-3094.
Wang, T. L. et al., "Digital karyotyping." *Proc Natl Acad Sci USA*, Dec. 10, 2002;99(25):16156-16161.
Waterston, R. H. et al., "Initial sequencing and comparative analysis of the mouse genome," *Nature*; Dec. 5, 2002;420:520-562.
Yang et al., "High fidelity PCR with an off/on switch mediated by proofreading polymerases combining with phosphorothioate-modified primer," *Biochem Biophys Res Commun*, Jan. 6, 2005;328:265-272.
Zhang et al., "Single-base discrimination mediated by proofreading 3' phosphorothioate-modified primers," *Mol Biotechnol*, Nov. 2003;25(3):223-227.
Zhu et al., "Single molecule profiling of alternative pre-mRNA splicing," *Science*, Aug. 8, 2003; 301:836-838.
Zirvi et al., "Improved fidelity of thermostable ligases for detection of microsatellite repeat sequences using nucleoside analogs," *Nucleic Acids Res*, Oct. 17, 1999;27(24):e41; 7 pgs.
Zirvi et al., "Ligase-based detection of mononucleotide repeat sequences," *Nucleic Acids Res*, Oct. 18, 1999;27(24):e40; 8 pgs.
Kim et al., "Cloning, Nucleotide Sequence, and Expression of the DNA Ligase-encoding Gene from *Thermus filiformis," Molecules and Cells*, 1998; 8(4):438-443.

* cited by examiner

Chromosome

| Chromosome | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
|---|---|---|---|---|---|---|---|---|---|---|---|---|---|---|---|---|---|---|---|---|---|---|---|---|
| 1 | 90% | 1.6% | 1.6% | 1.7% | 1.8% | 1.8% | 2.1% | 1.9% | 2.1% | 2.1% | 2.0% | 2.1% | 1.9% | 2.3% | 2.5% | 2.7% | 2.8% | 2.1% | 3.9% | 2.5% | 2.7% | 3.3% | 1.8% | 4.4% |
| 2 | 1.6% | 91% | 1.5% | 1.5% | 1.6% | 1.7% | 1.8% | 1.7% | 2.0% | 2.0% | 1.8% | 1.9% | 2.0% | 2.3% | 2.4% | 2.5% | 2.6% | 2.2% | 3.2% | 2.3% | 3.0% | 3.7% | 1.9% | 3.9% |
| 3 | 1.3% | 1.2% | 93% | 1.4% | 1.4% | 1.5% | 1.6% | 1.5% | 1.8% | 1.7% | 1.7% | 1.8% | 1.7% | 1.9% | 2.0% | 2.2% | 2.2% | 1.8% | 2.8% | 2.1% | 2.3% | 2.6% | 1.6% | 3.3% |
| 4 | 1.3% | 1.2% | 1.3% | 93% | 1.3% | 1.4% | 1.5% | 1.5% | 1.6% | 1.6% | 1.6% | 1.6% | 1.6% | 1.8% | 1.8% | 1.9% | 1.9% | 1.7% | 2.4% | 1.9% | 2.1% | 2.3% | 1.5% | 3.3% |
| 5 | 1.2% | 1.1% | 1.2% | 1.2% | 92% | 1.4% | 1.4% | 1.4% | 1.6% | 1.5% | 1.5% | 1.6% | 1.5% | 1.7% | 1.9% | 1.9% | 2.0% | 1.6% | 2.6% | 1.9% | 2.1% | 2.3% | 1.5% | 3.0% |
| 6 | 1.2% | 1.1% | 1.2% | 1.2% | 1.3% | 93% | 1.4% | 1.4% | 1.6% | 1.5% | 1.5% | 1.5% | 1.5% | 1.7% | 1.8% | 1.8% | 2.0% | 1.6% | 2.6% | 1.9% | 2.0% | 2.3% | 1.4% | 2.9% |
| 7 | 1.3% | 1.1% | 1.2% | 1.2% | 1.2% | 1.3% | 80% | 1.3% | 1.6% | 1.5% | 1.5% | 1.7% | 1.4% | 1.7% | 1.8% | 2.0% | 2.2% | 1.6% | 2.8% | 2.0% | 2.2% | 2.6% | 1.4% | 2.8% |
| 8 | 1.0% | 0.9% | 1.0% | 1.1% | 1.1% | 1.1% | 1.2% | 93% | 1.3% | 1.3% | 1.3% | 1.4% | 1.3% | 1.5% | 1.6% | 1.6% | 1.7% | 1.4% | 2.2% | 1.6% | 1.7% | 2.0% | 1.2% | 2.6% |
| 9 | 0.9% | 1.0% | 0.9% | 1.0% | 0.9% | 1.0% | 1.1% | 1.0% | 85% | 1.2% | 1.1% | 1.2% | 1.2% | 1.4% | 1.5% | 1.5% | 1.6% | 1.4% | 2.1% | 1.6% | 1.9% | 2.2% | 1.0% | 2.4% |
| 10 | 1.0% | 0.9% | 1.0% | 1.0% | 1.0% | 1.1% | 1.2% | 1.1% | 1.3% | 90% | 1.2% | 1.3% | 1.2% | 1.5% | 1.6% | 1.8% | 1.8% | 1.4% | 2.3% | 1.6% | 1.8% | 2.5% | 1.1% | 2.8% |
| 11 | 1.0% | 0.9% | 1.0% | 1.0% | 1.1% | 1.1% | 1.2% | 1.2% | 1.3% | 1.3% | 92% | 1.3% | 1.2% | 1.4% | 1.5% | 1.7% | 1.7% | 1.3% | 2.3% | 1.6% | 1.7% | 2.1% | 1.1% | 2.6% |
| 12 | 1.1% | 1.0% | 1.1% | 1.1% | 1.1% | 1.2% | 1.3% | 1.2% | 1.4% | 1.3% | 1.3% | 92% | 1.3% | 1.6% | 1.7% | 1.8% | 1.9% | 1.4% | 2.4% | 1.8% | 1.9% | 2.3% | 1.2% | 2.6% |
| 13 | 0.7% | 0.6% | 0.7% | 0.7% | 0.7% | 0.7% | 0.8% | 0.8% | 0.9% | 0.8% | 0.8% | 0.9% | 95% | 1.0% | 1.1% | 1.0% | 1.1% | 1.2% | 1.4% | 1.1% | 2.0% | 1.5% | 0.8% | 2.1% |
| 14 | 0.7% | 0.7% | 0.7% | 0.7% | 0.7% | 0.8% | 0.9% | 0.8% | 1.0% | 0.9% | 0.9% | 1.0% | 1.0% | 93% | 1.3% | 1.2% | 1.3% | 1.1% | 1.6% | 1.2% | 1.6% | 3.2% | 0.9% | 2.0% |
| 15 | 0.7% | 0.6% | 0.7% | 0.6% | 0.7% | 0.7% | 0.8% | 0.8% | 0.9% | 0.9% | 0.8% | 0.9% | 0.9% | 1.1% | 91% | 1.3% | 1.3% | 1.1% | 1.8% | 1.2% | 1.5% | 1.7% | 0.8% | 1.8% |
| 16 | 0.7% | 0.7% | 0.7% | 0.7% | 0.7% | 0.7% | 0.9% | 0.8% | 1.0% | 1.0% | 0.9% | 0.9% | 0.8% | 1.0% | 1.3% | 90% | 1.4% | 1.0% | 2.0% | 1.3% | 1.3% | 2.0% | 0.8% | 2.0% |
| 17 | 0.8% | 0.7% | 0.8% | 0.7% | 0.8% | 0.8% | 1.0% | 0.9% | 1.0% | 1.0% | 0.9% | 1.0% | 0.9% | 1.1% | 1.3% | 1.4% | 88% | 1.1% | 2.2% | 1.4% | 1.4% | 2.0% | 0.8% | 1.7% |
| 18 | 0.5% | 0.6% | 0.5% | 0.5% | 0.6% | 0.6% | 0.6% | 0.6% | 0.7% | 0.7% | 0.6% | 0.7% | 0.9% | 0.9% | 1.0% | 0.9% | 1.0% | 95% | 1.1% | 0.9% | 2.5% | 1.3% | 0.6% | 1.5% |
| 19 | 0.7% | 0.6% | 0.7% | 0.6% | 0.7% | 0.7% | 0.9% | 0.8% | 1.0% | 0.9% | 0.9% | 0.9% | 0.8% | 1.0% | 1.3% | 1.4% | 1.5% | 0.9% | 86% | 1.3% | 1.3% | 2.0% | 0.8% | 1.6% |
| 20 | 0.5% | 0.4% | 0.5% | 0.5% | 0.5% | 0.5% | 0.7% | 0.6% | 0.7% | 0.6% | 0.6% | 0.7% | 0.6% | 0.7% | 0.8% | 0.9% | 1.0% | 0.7% | 1.3% | 94% | 1.0% | 1.3% | 0.5% | 1.3% |
| 21 | 0.3% | 0.3% | 0.3% | 0.3% | 0.3% | 0.3% | 0.3% | 0.3% | 0.4% | 0.4% | 0.3% | 0.4% | 0.6% | 0.5% | 0.6% | 0.5% | 0.5% | 1.1% | 0.6% | 0.5% | 96% | 0.9% | 0.3% | 1.0% |
| 22 | 0.4% | 0.4% | 0.3% | 0.3% | 0.3% | 0.4% | 0.4% | 0.4% | 0.5% | 0.5% | 0.4% | 0.5% | 0.5% | 0.8% | 0.6% | 0.8% | 0.8% | 0.5% | 1.0% | 0.7% | 0.9% | 89% | 0.4% | 1.3% |
| X | 1.2% | 1.1% | 1.2% | 1.2% | 1.3% | 1.3% | 1.4% | 1.3% | 1.5% | 1.4% | 1.4% | 1.5% | 1.5% | 1.7% | 1.7% | 1.7% | 1.8% | 1.6% | 2.2% | 1.7% | 2.0% | 2.1% | 89% | 28.6% |
| Y | 0.3% | 0.2% | 0.2% | 0.2% | 0.2% | 0.2% | 0.3% | 0.3% | 0.3% | 0.3% | 0.3% | 0.3% | 0.3% | 0.3% | 0.4% | 0.5% | 0.3% | 0.3% | 0.5% | 0.4% | 0.6% | 0.7% | 3.3% | 64% |
| Good Tags | **80%** | **82%** | **83%** | **83%** | **82%** | **83%** | **78%** | **82%** | **74%** | **79%** | **81%** | **81%** | **84%** | **80%** | **76%** | **74%** | **74%** | **83%** | **68%** | **81%** | **80%** | **71%** | **76%** | **36%** |
| Total | 80% | | | | | | | | | | | | | | | | | | | | | | | |

Figure 2

Shendure et al., September 2005 *Science* 309:1728-1732.

Figure 11

Cyclic Ligation Nonamers

3′ N*N*N*N*ANNIN-Cy3 5′

3′ N*N*N*N*TNNIN-Cy5 5′

3′ N*N*N*N*CNNIN-TxRed 5′

3′ N*N*N*N*GNNIN-FITC 5′

Image from Li et al. (2006) Nat Methods.

Figure 27

Unique Identification of Ends

| | Total mate pair sequence read | | | | | | |
|---|---|---|---|---|---|---|---|
| Hits | 14base | 16base | 18base | 20base | 22 base | 24base | 26base |
| 1 | 0.0% | 1.0% | 14.0% | 65.0% | 85.3% | 90.8% | 92.7% |
| 2 | 0.0% | 2.0% | 16.3% | 16.4% | 6.8% | 3.5% | 2.7% |
| 3 | 0.0% | 1.3% | 11.3% | 5.3% | 1.6% | 0.8% | 0.5% |
| 4 | 0.0% | 1.0% | 9.7% | 2.5% | 1.0% | 0.3% | 0.4% |
| 5 | 0.0% | 0.7% | 6.3% | 1.5% | 0.7% | 0.3% | 0.2% |
| 6 | 0.0% | 1.0% | 6.3% | 0.9% | 0.4% | 0.3% | 0.2% |
| 7 | 0.3% | 0.3% | 5.7% | 0.6% | 0.2% | 0.2% | 0.1% |
| 8 | 0.0% | 0.3% | 3.3% | 0.6% | 0.2% | 0.1% | 0.1% |
| 9 | 0.0% | 1.0% | 2.3% | 0.6% | 0.0% | 0.2% | 0.1% |
| 10 | 0.0% | 1.0% | 2.7% | 0.5% | 0.1% | 0.2% | 0.1% |

SNPs can be discerned too based on hybridization patterns.

5′ TTTACACTAGTCTGAGATAGTCTATCAG(Cont)
CATCAGTAGTGCTGCGTCTATATTATATAT 3′

SEQUENCE LISTING

```
<160> NUMBER OF SEQ ID NOS: 37

<210> SEQ ID NO 1
<211> LENGTH: 47
<212> TYPE: DNA
<213> ORGANISM: artificial
<220> FEATURE:
<223> OTHER INFORMATION: synthetic library preparation primer

<400> SEQUENCE: 1

aaccactacg cctccgcttt cctctctatg tctactagtc aacggct                47


<210> SEQ ID NO 2
<211> LENGTH: 46
```

-continued

<212> TYPE: DNA
<213> ORGANISM: artificial
<220> FEATURE:
<223> OTHER INFORMATION: synthetic library preparation primer

<400> SEQUENCE: 2
gccgttgact agtagacata gagaggaaag cggaggcgta gtggtt 46

<210> SEQ ID NO 3
<211> LENGTH: 47
<212> TYPE: DNA
<213> ORGANISM: artificial
<220> FEATURE:
<223> OTHER INFORMATION: synthetic library preparation primer

<400> SEQUENCE: 3
atatgtcaac tgccccgggt tcctcattca ctcatgacta ctgaagt 47

<210> SEQ ID NO 4
<211> LENGTH: 46
<212> TYPE: DNA
<213> ORGANISM: artificial
<220> FEATURE:
<223> OTHER INFORMATION: synthetic library preparation primer

<400> SEQUENCE: 4
cttcagtagt catgagtgaa tgaggaaccc ggggcagttg acatat 46

<210> SEQ ID NO 5
<211> LENGTH: 21
<212> TYPE: DNA
<213> ORGANISM: artificial
<220> FEATURE:
<223> OTHER INFORMATION: synthetic library preparation primer

<400> SEQUENCE: 5
aaccactacg cctccgcttt c 21

<210> SEQ ID NO 6
<211> LENGTH: 17
<212> TYPE: DNA
<213> ORGANISM: artificial
<220> FEATURE:
<223> OTHER INFORMATION: synthetic library preparation primer

<400> SEQUENCE: 6
ctgccccggg ttcctca 17

<210> SEQ ID NO 7
<211> LENGTH: 66
<212> TYPE: DNA
<213> ORGANISM: artificial
<220> FEATURE:
<223> OTHER INFORMATION: synthetic emulsion primer

<400> SEQUENCE: 7
tttttttttt tttttttttt tttttttttt ttttttaacc actacgcctc cgctttcctc 60
tctatg 66

<210> SEQ ID NO 8
<211> LENGTH: 112
<212> TYPE: DNA
<213> ORGANISM: artificial
<220> FEATURE:
<223> OTHER INFORMATION: synthetic emulsion primer

<400> SEQUENCE: 8
tttttttttt tttttttttt tttttttttt tttttttttt tttttttttt tttttttttt 60
tttttttttt tttttttttt tttatatgtc aactgccccg ggttcctcat tc 112

<210> SEQ ID NO 9
<211> LENGTH: 24
<212> TYPE: DNA
<213> ORGANISM: artificial
<220> FEATURE:
<223> OTHER INFORMATION: synthetic emulsion primer

<400> SEQUENCE: 9
aaccactacg cctccgcttt cctc 24

<210> SEQ ID NO 10
<211> LENGTH: 24
<212> TYPE: DNA
<213> ORGANISM: artificial
<220> FEATURE:
<223> OTHER INFORMATION: synthetic emulsion primer

<400> SEQUENCE: 10
atatgtcaac tgccccgggt tcct 24

<210> SEQ ID NO 11
<211> LENGTH: 28
<212> TYPE: DNA
<213> ORGANISM: artificial
<220> FEATURE:
<223> OTHER INFORMATION: synthetic capping oligonucleotide
<220> FEATURE:
<221> NAME/KEY: misc_feature
<222> LOCATION: (1)..(2)
<223> OTHER INFORMATION: n is a, c, g, or t

<400> SEQUENCE: 11
nntatcactc agactatact ctaaacca 28

<210> SEQ ID NO 12
<211> LENGTH: 21
<212> TYPE: DNA
<213> ORGANISM: artificial
<220> FEATURE:
<223> OTHER INFORMATION: synthetic capping oligonucleotide

<400> SEQUENCE: 12
tagagtatag tctgagtgat a 21

<210> SEQ ID NO 13
<211> LENGTH: 31
<212> TYPE: DNA
<213> ORGANISM: artificial
<220> FEATURE:
<223> OTHER INFORMATION: synthetic capping oligonucleotide

<400> SEQUENCE: 13
tctacatatt ctaccatcta cttatcacac a 31

<210> SEQ ID NO 14
<211> LENGTH: 28
<212> TYPE: DNA
<213> ORGANISM: artificial
<220> FEATURE:
<223> OTHER INFORMATION: synthetic capping oligonucleotide
<220> FEATURE:
<221> NAME/KEY: misc_feature
<222> LOCATION: (27)..(28)
<223> OTHER INFORMATION: n is a, c, g, or t

<400> SEQUENCE: 14
gataagtaga tggtagaata tgtagann 28

<210> SEQ ID NO 15
<211> LENGTH: 18
<212> TYPE: DNA
<213> ORGANISM: artificial
<220> FEATURE:
<223> OTHER INFORMATION: synthetic anchor primer

<400> SEQUENCE: 15
agccgttgac tagtagac 18

<210> SEQ ID NO 16
<211> LENGTH: 18
<212> TYPE: DNA
<213> ORGANISM: artificial
<220> FEATURE:
<223> OTHER INFORMATION: synthetic anchor primer

<400> SEQUENCE: 16
acttcagtag tcatgagt 18

<210> SEQ ID NO 17
<211> LENGTH: 21
<212> TYPE: DNA
<213> ORGANISM: artificial
<220> FEATURE:
<223> OTHER INFORMATION: synthetic anchor primer

<400> SEQUENCE: 17
tagagtatag tctgagtgat a 21

<210> SEQ ID NO 18
<211> LENGTH: 26
<212> TYPE: DNA
<213> ORGANISM: artificial
<220> FEATURE:
<223> OTHER INFORMATION: synthetic anchor primer

<400> SEQUENCE: 18
gataagtaga tggtagaata tgtaga 26

<210> SEQ ID NO 19
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (1)..(1)
<223> OTHER INFORMATION: sequence contains a 5' fluorescent Cy5 dye
<220> FEATURE:
<221> NAME/KEY: misc_feature
<222> LOCATION: (2)..(8)
<223> OTHER INFORMATION: n is a, c, g, or t

<400> SEQUENCE: 19 nnnnnnnnt 9

<210> SEQ ID NO 20
<211> LENGTH: 9
<212> TYPE: DNA

<213> ORGANISM: artificial
<220> FEATURE:
<223> OTHER INFORMATION: synthetic sequencing nonamer
<220> FEATURE:
<221> NAME/KEY: misc_feature
<222> LOCATION: (1)..(1)
<223> OTHER INFORMATION: sequence contains a 5' fluorescent Cy3 dye
<220> FEATURE:
<221> NAME/KEY: misc_feature
<222> LOCATION: (2)..(8)
<223> OTHER INFORMATION: n is a, c, g, or t

<400> SEQUENCE: 20 nnnnnnnna 9

<210> SEQ ID NO 21
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (1)..(1)
<223> OTHER INFORMATION: sequence contains a 5' fluorescent TexasRed dye
<220> FEATURE:
<221> NAME/KEY: misc_feature
<222> LOCATION: (2)..(8)
<223> OTHER INFORMATION: n is a, c, g, or t

<400> SEQUENCE: 21 nnnnnnnnc 9

<210> SEQ ID NO 22
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (1)..(1)
<223> OTHER INFORMATION: sequence contains a 5' fluorescent FAM dye
<220> FEATURE:
<221> NAME/KEY: misc_feature
<222> LOCATION: (2)..(8)
<223> OTHER INFORMATION: n is a, c, g, or t

<400> SEQUENCE: 22 nnnnnnnng 9

<210> SEQ ID NO 23
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (2)..(8)
<223> OTHER INFORMATION: n is a, c, g, or t
<220> FEATURE:
<221> NAME/KEY: misc_feature
<222> LOCATION: (9)..(9)
<223> OTHER INFORMATION: sequence contains a 3' fluorescent Cy5 dye

<400> SEQUENCE: 23 tnnnnnnnn 9

<210> SEQ ID NO 24
<211> LENGTH: 9

-continued

<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (2)..(8)
<223> OTHER INFORMATION: n is a, c, g, or t
<220> FEATURE:
<221> NAME/KEY: misc_feature
<222> LOCATION: (9)..(9)
<223> OTHER INFORMATION: sequence contains a 3' fluorescent Cy3 dye

<400> SEQUENCE: 24 annnnnnnn 9

<210> SEQ ID NO 25
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (2)..(8)
<223> OTHER INFORMATION: n is a, c, g, or t
<220> FEATURE:
<221> NAME/KEY: misc_feature
<222> LOCATION: (9)..(9)
<223> OTHER INFORMATION: sequence contains a 3' fluorescent TexasRed dye

<400> SEQUENCE: 25 cnnnnnnnn 9

<210> SEQ ID NO 26
<211> LENGTH: 9
<212> TYPE: DNA
<213> ORGANISM: artificial
<220> FEATURE:
<223> OTHER INFORMATION: synthetic sequencing nonamer
<220> FEATURE:
<221> NAME/KEY: misc_feature
<222> LOCATION: (2)..(8)
<223> OTHER INFORMATION: n is a, c, g, or t
<220> FEATURE:
<221> NAME/KEY: misc_feature
<222> LOCATION: (9)..(9)
<223> OTHER INFORMATION: sequence contains a 3' fluorescent FAM dye

<400> SEQUENCE: 26 gnnnnnnnn 9

<210> SEQ ID NO 27
<211> LENGTH: 9
<212> TYPE: DNA
<213> ORGANISM: artificial
<220> FEATURE:
<223> OTHER INFORMATION: synthetic ligation nonamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (1)..(1)
<223> OTHER INFORMATION: sequence contains a 5' fluorescent Cy3 dye
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)

<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t

<400> SEQUENCE: 27 nnnnannnn 9

<210> SEQ ID NO 28
<211> LENGTH: 9
<212> TYPE: DNA
<213> ORGANISM: artificial
<220> FEATURE:
<223> OTHER INFORMATION: synthetic ligation nonamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (1)..(1)
<223> OTHER INFORMATION: sequence contains a 5' fluorescent Cy5 dye
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t

<400> SEQUENCE: 28 nnnntnnnn 9

<210> SEQ ID NO 29
<211> LENGTH: 9
<212> TYPE: DNA
<213> ORGANISM: artificial
<220> FEATURE:
<223> OTHER INFORMATION: synthetic ligation nonamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (1)..(1)
<223> OTHER INFORMATION: sequence contains a 5' fluorescent TexasRed dye
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t

<400> SEQUENCE: 29 nnnncnnnn 9

<210> SEQ ID NO 30
<211> LENGTH: 9
<212> TYPE: DNA
<213> ORGANISM: artificial
<220> FEATURE:
<223> OTHER INFORMATION: synthetic ligation nonamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (1)..(1)
<223> OTHER INFORMATION: sequence contains a 5' fluorescent FITC dye
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t

<400> SEQUENCE: 30 nnnngnnnn 9

<210> SEQ ID NO 31
<211> LENGTH: 15
<212> TYPE: DNA
<213> ORGANISM: artificial
<220> FEATURE:
<223> OTHER INFORMATION: synthetic anchor primer

<400> SEQUENCE: 31
acucuagcug acuag 15

<210> SEQ ID NO 32
<211> LENGTH: 35
<212> TYPE: DNA
<213> ORGANISM: artificial
<220> FEATURE:
<223> OTHER INFORMATION: bead-immobilized template strand
<220> FEATURE:
<221> NAME/KEY: misc_feature
<222> LOCATION: (5)..(20)
<223> OTHER INFORMATION: n is a, c, g, or t

<400> SEQUENCE: 32
gagtnnnnnn nnnnnnnnnn tgagatcgac tgatc 35

<210> SEQ ID NO 33
<211> LENGTH: 45
<212> TYPE: DNA
<213> ORGANISM: artificial
<220> FEATURE:
<223> OTHER INFORMATION: sample raw sequence data

<400> SEQUENCE: 33
atcgcatcga cgctccactc gaactgactg gctacgctcg cgccg 45

<210> SEQ ID NO 34
<211> LENGTH: 17
<212> TYPE: DNA
<213> ORGANISM: artificial
<220> FEATURE:
<223> OTHER INFORMATION: bead-immobilized template strand

<400> SEQUENCE: 34
atcgatcgat gtatatt 17

<210> SEQ ID NO 35
<211> LENGTH: 14
<212> TYPE: DNA
<213> ORGANISM: artificial
<220> FEATURE:
<223> OTHER INFORMATION: synthetic extended query oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 35
nnnnntnnnn cnnn 14

<210> SEQ ID NO 36
<211> LENGTH: 23
<212> TYPE: DNA
<213> ORGANISM: artificial
<220> FEATURE:
<223> OTHER INFORMATION: sample Sequencing-by-Hybridization template

<400> SEQUENCE: 36
tcgatgtcat gtcatgtact gat 23

<210> SEQ ID NO 37
<211> LENGTH: 58
<212> TYPE: DNA
<213> ORGANISM: artificial
<220> FEATURE:
<223> OTHER INFORMATION: sample probe analysis template

<400> SEQUENCE: 37
tttacactag tctgagatag tctatcagca tcagtagtgc tgcgtctata ttatatat 58

POLONY SEQUENCING METHODS

CROSS-REFERENCE TO RELATED APPLICATION

This application is the §371 U.S. National Stage of International Application No. PCT/US2010/051938, filed 8 Oct. 2010, which claims priority to U.S. Provisional Patent Application Ser. No. 61/250,209, filed Oct. 9, 2009, U.S. Provisional Patent Application Ser. No. 61/264,909, filed Nov. 30, 2009, and U.S. Provisional Patent Application Ser. No. 61/313,365, filed Mar. 12, 2010, each of which is hereby incorporated by reference in its entirety.

GOVERNMENT FUNDING

This invention was made with government support under R21 HG004350 awarded by the National Institutes of Health. The government has certain rights in the invention.

BACKGROUND

The resounding success of the Human Genome Project (HGP) clearly illustrates how early investments in developing cost-effective methods of biological data acquisition can have tremendous payoffs for the biomedical community. Over the course of a decade, through refinement, parallelization, and automation of established sequencing technologies, the HGP motivated a 100-fold reduction of sequencing costs, from $10 per finished base to $0.10 per finished base. Initially, the relevance and utility of sequencing and sequencing centers in the wake of the HGP was debated. However, now it is clear that the completion of the human genome marks the end-of-the-beginning, rather than the beginning-of-the-end, of the era of sequencing. The list of realized and potential applications for this type of high-throughput sequencing technology is rich and growing. DNA sequencing technology has the potential to significantly and substantially impact health care, both directly by providing diagnostic and prognostic markers for the clinical setting, and indirectly by accelerating the pace of basic and clinical biomedical research.

High-throughput technologies have succeeded by spatially and temporally increasing the amount of information that can be gathered, e.g., through miniaturization or rapid sample processing. The development of the polony technology is an excellent example of spatial compression. The concept of a polony has evolved over time, and in its current form, polonies allow the formation of millions to billions of distinguishable, immobilized, amplified clonal DNA molecules arising from individual DNA or RNA molecules via a single PCR reaction. The fact that polony technology utilizes only a single step to generate billions of "distinct clones" for sequencing leads this technology to replace the complex robotics required to handle the tens of thousands of cloning and PCR reactions that feed conventional high-throughput sequencing. The development of BEAMing technology allows for further spatial compression.

SUMMARY OF THE INVENTION

We describe ultra-high throughput polony genome sequencing that can permit, for example, generating raw data to re-sequencing the human genome in about one week (including library prep and sequencing) at a reasonable cost. The methods described herein include one or more of the following: (1) increasing polony sequencing read length, (2) improving library construction and emulsions protocols, (3)

increasing bead density and/or moving to alternative clonal implication strategies (other than emulsion PCR or ePCR), and (4) extending software capabilities to allow SNP calls from our new sequencing raw data.

In one aspect, the invention provides a method that includes amplifying at least a portion of a nucleic acid molecule to form a polony; and sequencing at least 12 contiguous nucleic acid residues of the nucleic acid molecule.

In another aspect, the invention provides a method for producing a polynucleotide library. Generally, the method includes fragmenting a nucleic acid molecule, thereby producing a plurality of nucleic acid fragments, ligating a first end PCR primer to a first end of at least one fragment, and a second end PCR primer to a second end of the at least one fragment, wherein the PCR primers comprise a recognition site for a restriction enzyme that cuts remotely from its recognitions site; and amplifying the digested fragment.

In another aspect, the invention provides an alternative method for producing a polynucleotide library. Generally, this method includes digesting a double-stranded nucleic acid molecule, thereby producing a plurality of double-stranded nucleic acid fragments; adding an adapter comprising a PCR primer to each end of at least one fragment; circularizing the at least one fragment; nicking each strand of the circularized fragment; digesting a plurality of nucleotide bases of each strand at the nick, thereby creating an enlarged nick site; digesting the single strand at each enlarged nick site of the circularized fragment, thereby creating a post-hybridization fragment comprising the hybridized primers; ligating a first end PCR primer to a first end of the post-hybridization fragment, and a second end PCR primer to a second end of the post-hybridization fragment, thereby defining a first amplifiable polynucleotide between the first end PCR primer and the hybridized primers, and a second amplifiable polynucleotide between the second end PCR primer and the hybridized primers; and amplifying at least a portion of least one amplifiable polynucleotide.

In another aspect, the invention provides a method for obtaining the sequence of a polynucleotide. Generally, the method includes providing a polynucleotide library comprising a plurality of polynucleotide fragments; providing a substrate comprising an addressable array of polynucleotide fragments having known nucleotide sequences; contacting at least a portion of the library polynucleotide fragments with the substrate under conditions suitable to allow the library polynucleotide fragments to hybridize with a complementary substrate polynucleotide fragment; detecting the hybridizations; and assigning to the library polynucleotide fragment a nucleic acid sequences that is the complement of the substrate polynucleotide fragment to which it hybridized.

In another aspect, the invention provides an alternative method for obtaining the sequence of a polynucleotide. Generally, this method includes providing a polynucleotide library comprising a plurality of polynucleotide fragments; sequentially hybridizing a plurality of probes having known nucleic acid sequences to at least a portion of the polynucleotide library fragments; identifying at least a portion of the probes hybridized to the polynucleotide library fragments; and assigning to each hybridized fragment a nucleic acid sequence that is the complement of the nucleic acid sequence of the probe hybridized to the polynucleotide library fragment.

In another aspect, the invention provides an alternative method for obtaining the sequence of a polynucleotide. Generally, this method includes providing a polynucleotide library comprising a plurality of polynucleotide fragments; attaching at least one fragment to a substrate; annealing an anchor primer to the at least one fragment; ligating a primer-extending oligonucleotide to the anchor primer, thereby extending the anchor primer; and performing a sequencing method from the extended anchor primer.

In another aspect, the invention provides another alternative method for obtaining the sequence of a polynucleotide. Generally, this method includes a combination of sequencing strategies and includes providing a polynucleotide library comprising a plurality of polynucleotide fragments; sequencing at least five nucleotides of at least one end of the fragment; and performing Sequencing-by-Hybridization to determine the nucleotide sequence of at least a portion of the remainder of the fragment.

For any of the methods of obtaining the nucleotide sequence of a polynucleotide, the polynucleotide library may be provided using one or more of the methods of providing a polynucleotide library described herein.

In yet another aspect, the invention provides a method of identifying a subject at risk for a condition indicated by a known nucleic acid sequence. Generally, the method includes obtaining a biological sample from a subject comprising genomic DNA; fragmenting the genomic DNA; sequencing at least a portion of the genomic DNA according to any embodiment of the method summarized above, thereby determining whether the genomic DNA in the biological sample comprises the known nucleic acid sequence; and identifying the subject as at risk for the condition if the genomic DNA in the biological sample comprises the known nucleic acid sequence.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2: Whole genome simulations for $381\times10^6$ reads of mate paired 13 bp tags separated by 1000±300 bp. The columns in the figure indicate the chromosome where the tags were generated and the rows indicated the chromosome for which the tag matched. The highlighted cells along the diagonal indicates the percent of tags from a chromosome that uniquely mapped correctly to the same chromosome (i.e., the result if the sequencing was performed on flow sorted chromosomes). All other rows indicate the percent of tags that incorrectly matched a different chromosome. The bottom row ("Good Tags") indicates the final percentage of tags that correctly matched the given chromosome. And the total at the bottom is the final percentage of correctly mapped tags. The "Good Tags" number is smaller than the number on the diagonal because a correctly mapped tag to the correct chromosome may still be a "bad" tag if it incorrectly matches another chromosome. The final bottom number indicated the total percent of tags that correctly matched. Therefore, with 13 bp paired reads, we will correctly map 80% of the tags. Based on an extrapolation of the chromosome simulations, this will provide ~85% sequence coverage. Additionally, we obtain very good coverage of Chromosome 13 (83% tags matching correctly) and very poor coverage of the Y Chromosome (36% of tags matching correctly). The numbers are improved with longer reads: 14 bp reads=86% total tags matching correctly; 15 bp reads=89% total tags matching; 16 bp reads=90% total tags matching.

FIG. 11. Deoxyinosine nonamer design. The deoxyinosine and fixed base can be placed anywhere in the nonamer. Endonuclease V cleaves the second phosphodiester bond 3' from deoxyinosine. Asterisks denote phosphorothiate linkage that protects from Endo V cleavage. The nonamers shown reflect SEQ ID NO:27, SEQ ID NO: 28, SEQ ID NO:29, and SEQ ID NO:30.

that has been sequencing for a position already can have its signal cleaved and sequenced again with the position shifted, thus extending the sequence length.

Figure 13:
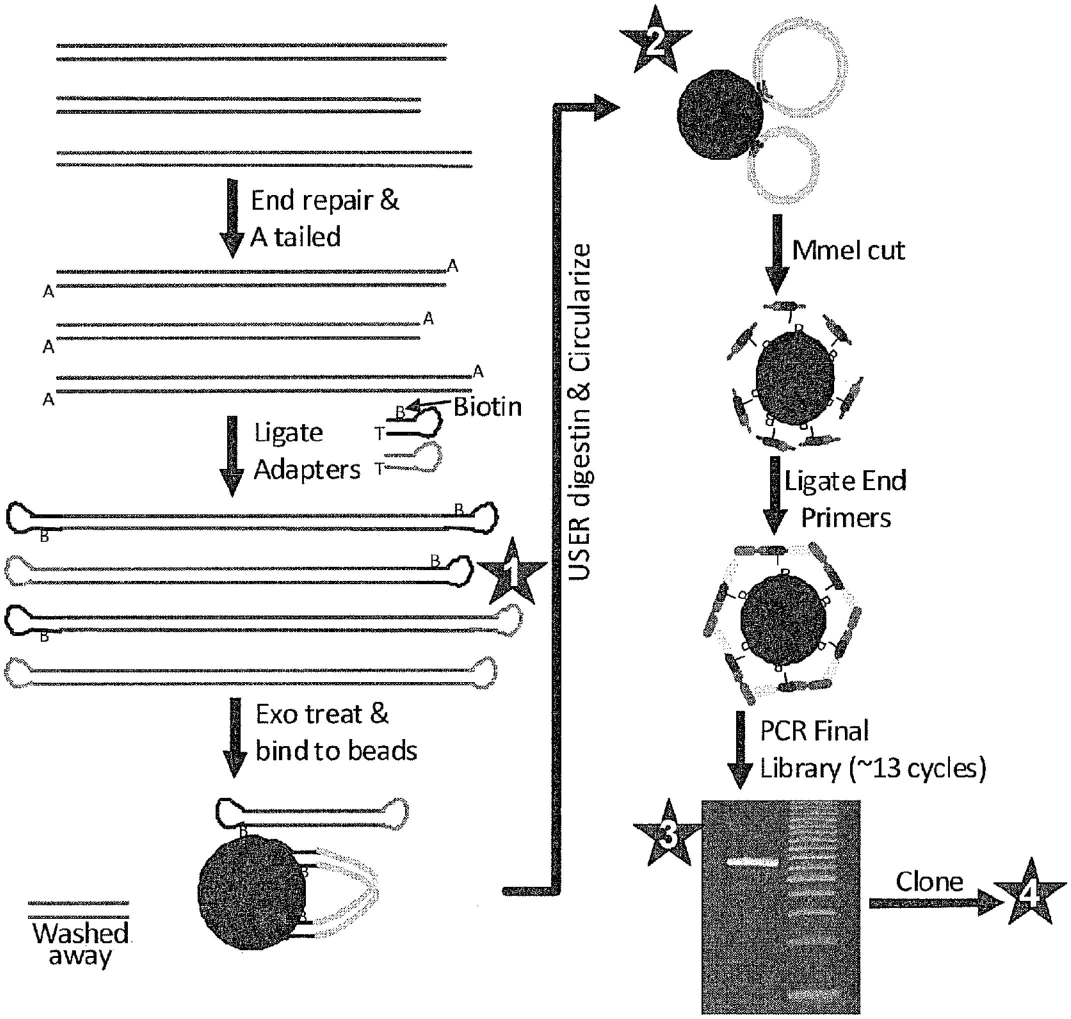

FIG. 13. A schematic diagram illustrating Library Preparation. Sheared DNA is end-repaired and A-tailed. Hairpin adaptors are ligated to the end of the fragments. The excess material is digested with exonuclease, where the fragments with hairpins on the ends are protected. The fragments are bound to beads to prevent unpaired libraries. The hairpins are removed by digesting dU in the primers, which leaves compatible ends. The molecules are circularized. Next, the circularized libraries are digested with MmeI and end adaptors are ligated to the fragments. Finally, 13-23 cycles of PCR are performed to generate the final library, which is verified on a diagnostic gel. Quality control (QC) steps are shown as numbered stars.

Figure 14:
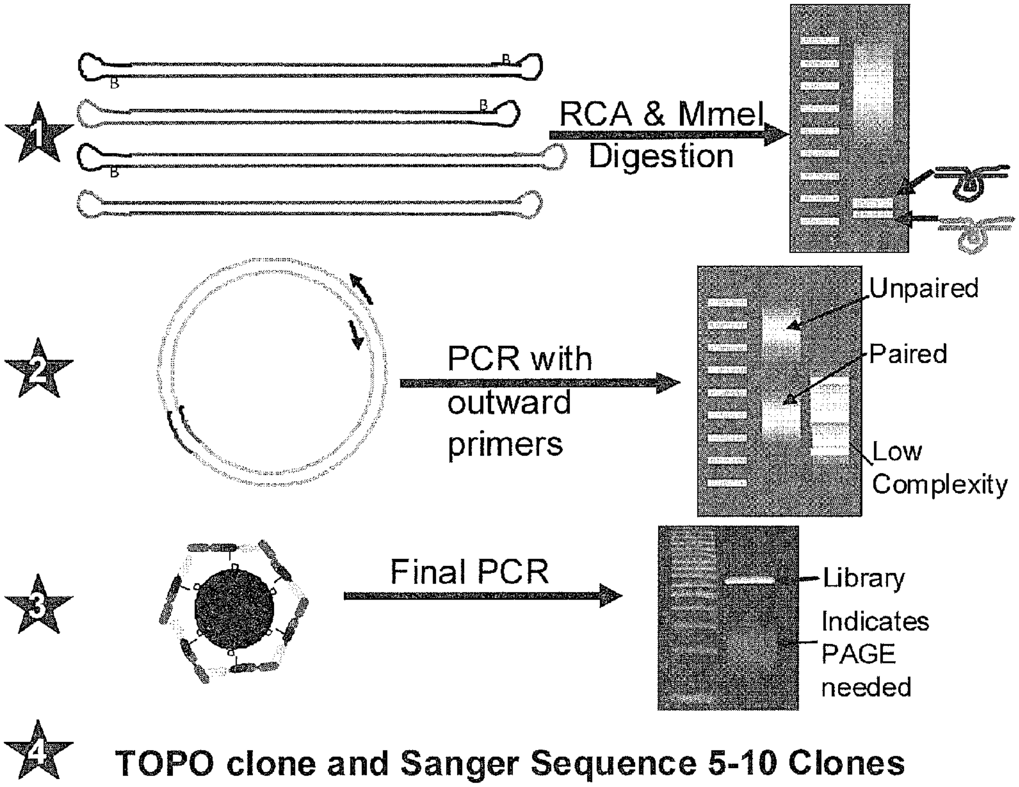

FIG. 14. A schematic diagram illustrating library preparation quality control steps.

Figure 15:
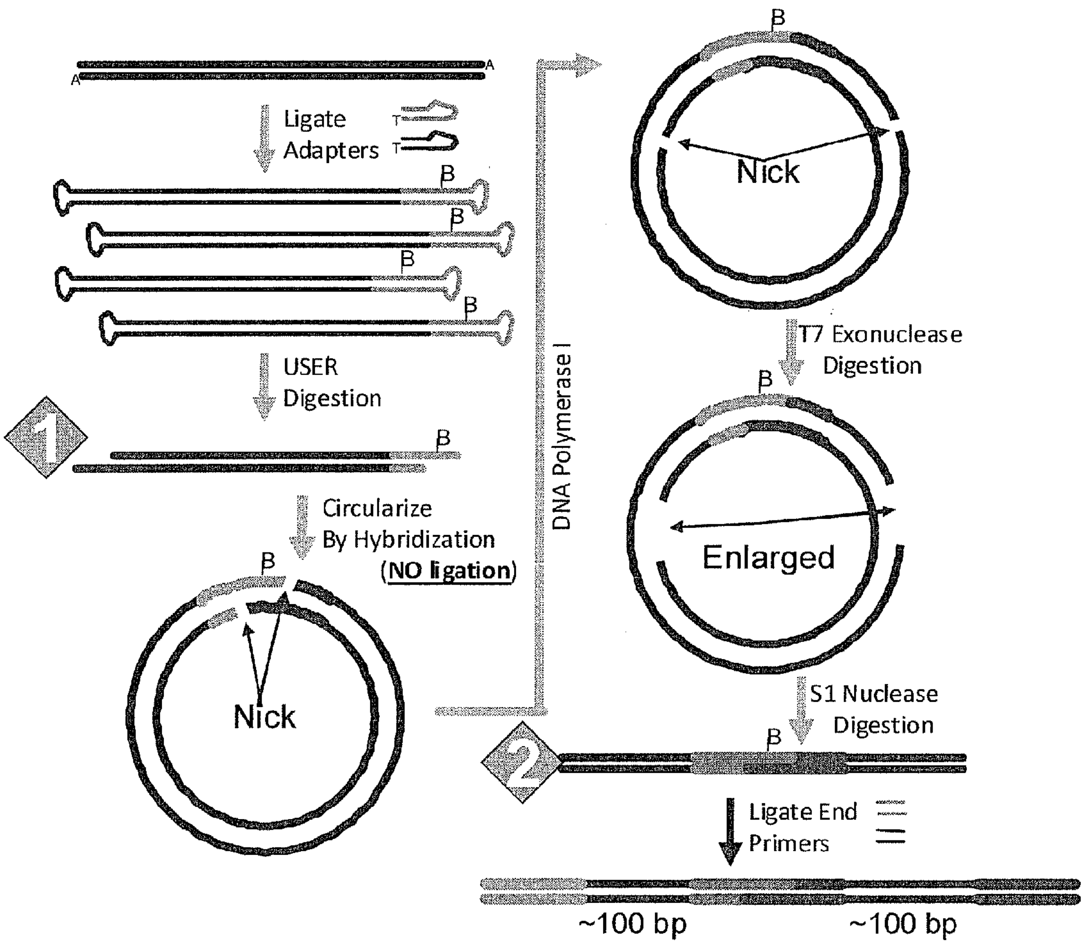

FIG. 15. A schematic diagram illustrating long mate pair tags protocol. The protocol involves two options for binding to beads. (1) Binding before circularization, thus inhibiting unpaired tags, as it has for a restriction enzyme generated libraries using the same circularization strategy. (2) Bead binding, which permits unpaired tags. However, with potential reads of 50+ bases per tag we can easily identify unpaired tags and compensate for this in the final analysis.

Figure 16:
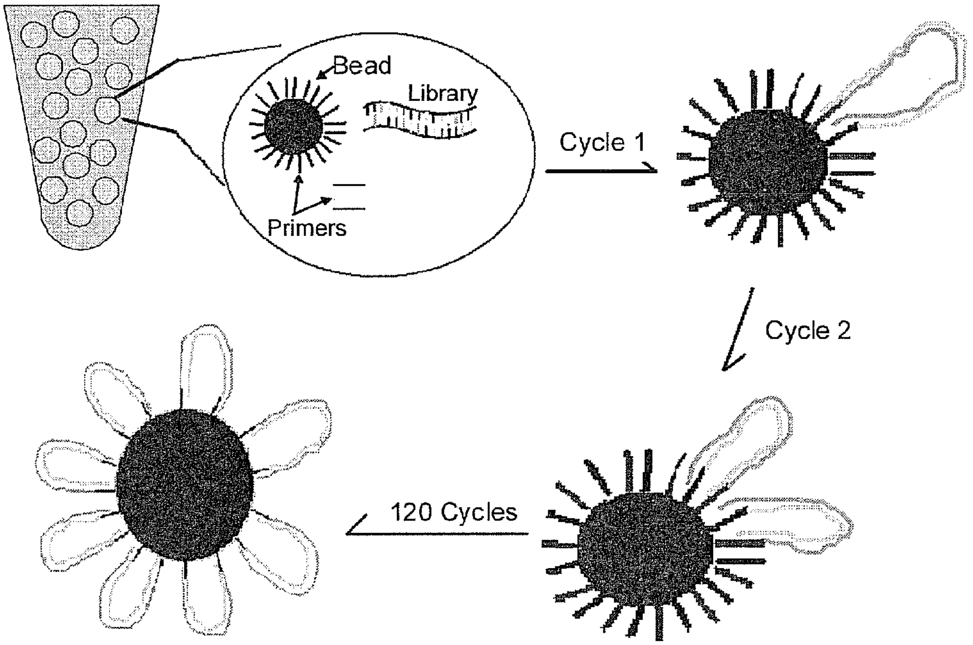

FIG. 16. A schematic diagram illustrating dual primer emulsion PCR. Dual primer ePCR or DPePCR is similar to regular ePCR, except both primers are on the bead in the same concentration and both primers are free in solution at the same concentration. After normal ePCR cycling, the 5' end of both strands of the DNA coating the bead is attached to the bead.

Figure 17:
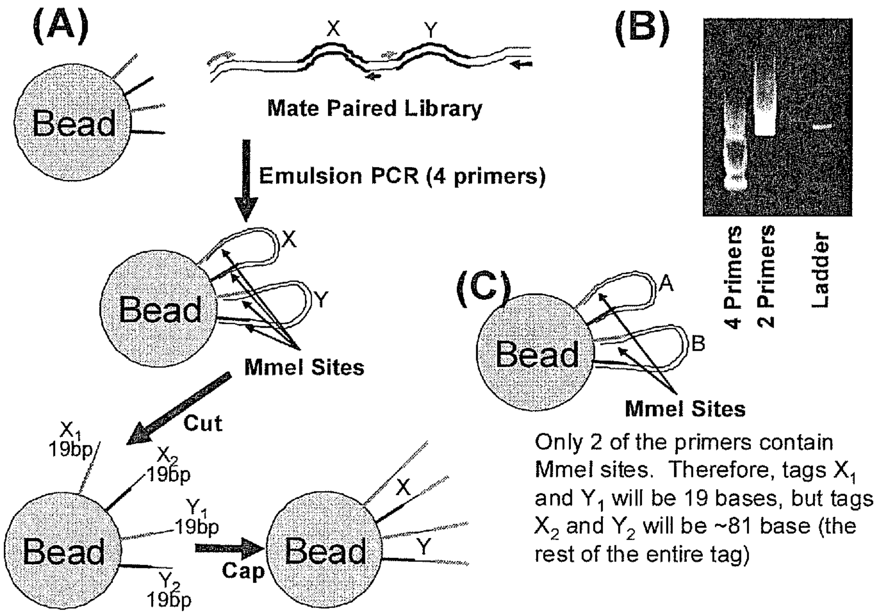

FIG. 17. A Schematic diagram illustrating Quad Primer ePCR (QPePCR). QPePCR is very similar to DPePCR, except each tag from a mate pair library becomes the fragment.

Panel (A) shows how paired ends from each mate pair can be sequenced. (B) Gel showing a Quad Primer PCR in solution. The anchor primers from sequencing reactions were used as the PCR primers. Note, relatively little ladder was loaded compared to the PCR lanes. (C) Alternatively, restriction enzyme sites may be incorporated on only one of each primer pair, allowing extended sequencing on the other end of the other strand.

Figure 18:
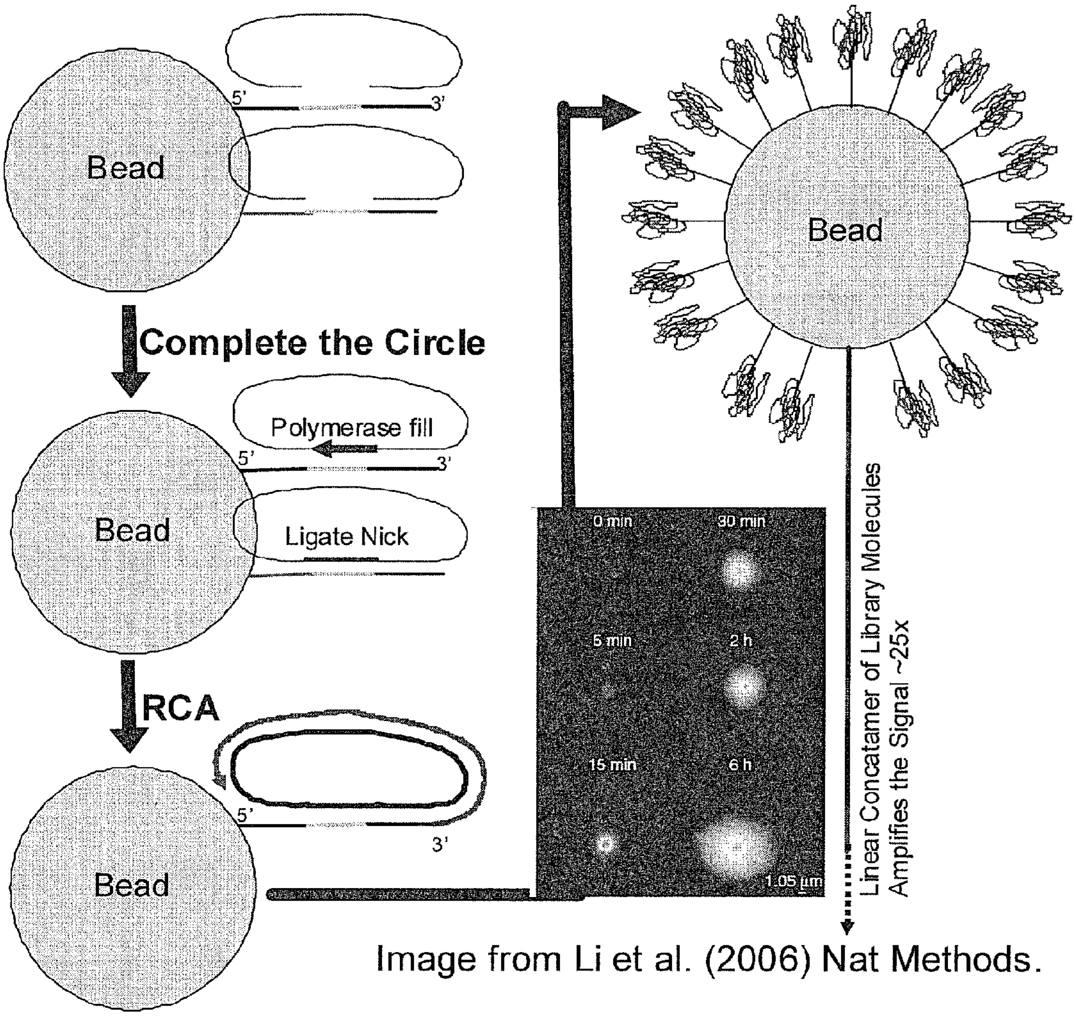

FIG. 18. A schematic diagram illustrating BEAMing UP technology.

Figure 19:
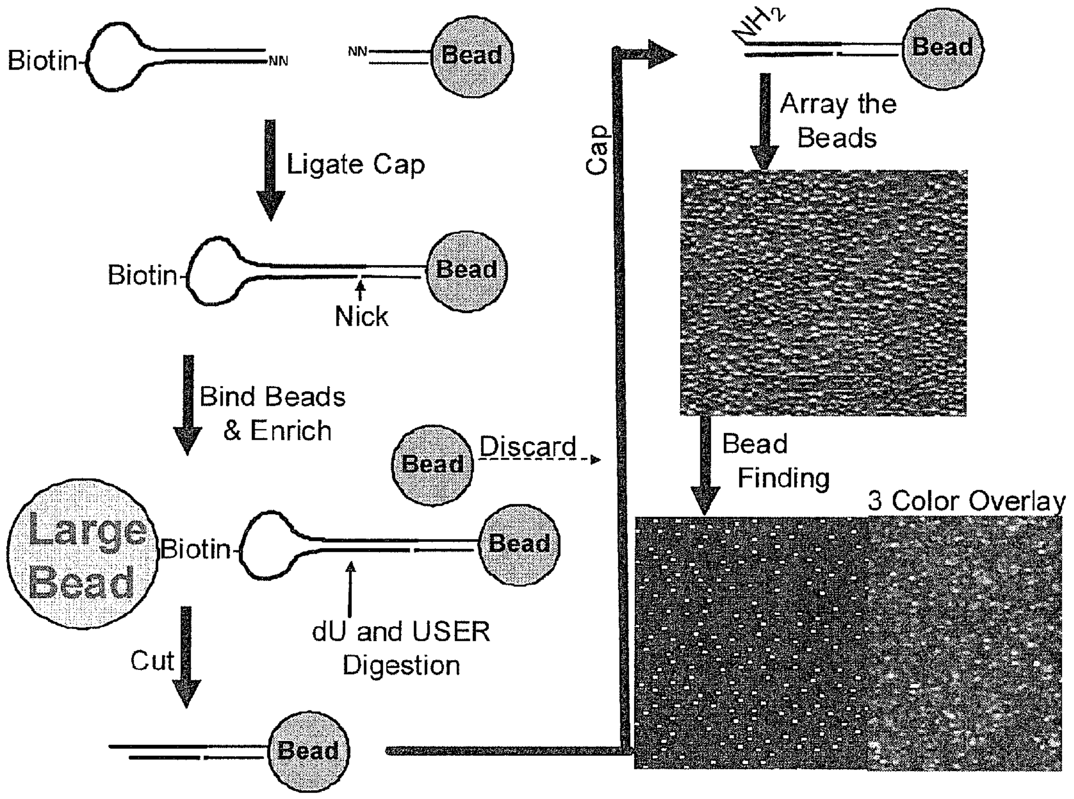

FIG. 19. A schematic diagram illustrating an enrichment strategy for DPePCR or QPePCR libraries.

Figure 20:
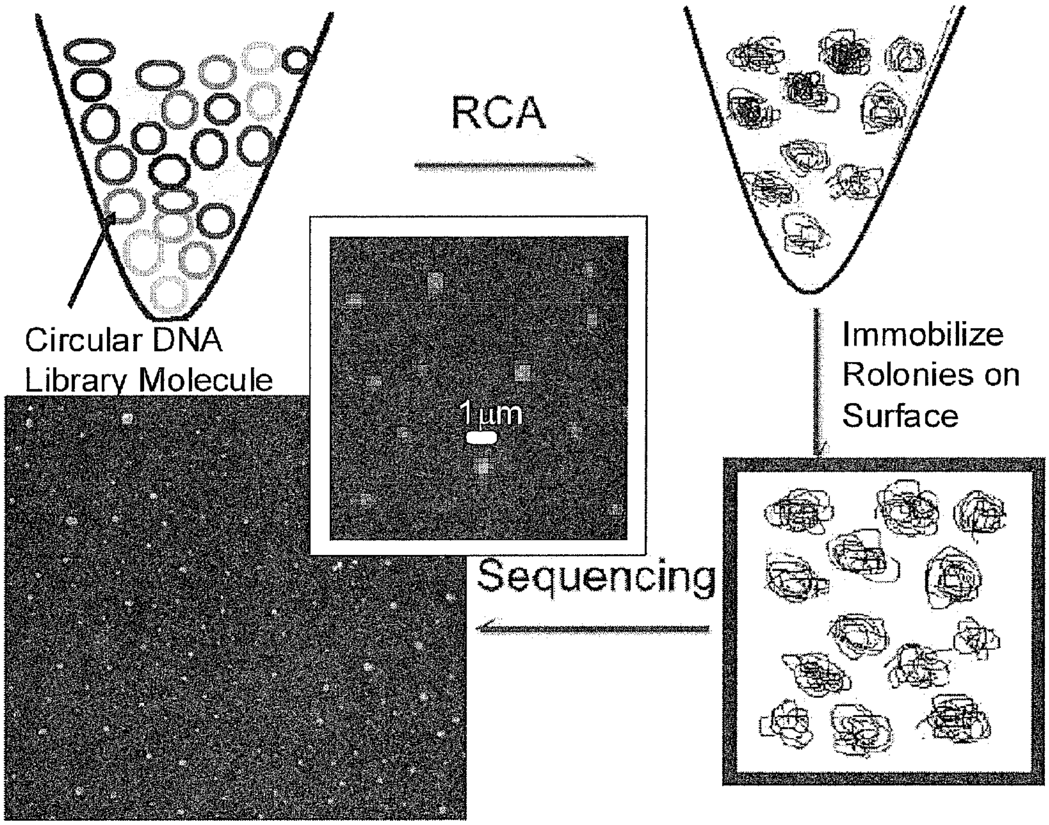

FIG. 20. A schematic diagram illustrating rolonies. Rolonies are made by first circularizing the library molecules. The circularized library is then amplified by linear RCA with a single specific primer. The resulting single stranded product forms into a condensed ball. The rolonies from each circular library molecule will remain distinct if the RCA is performed for a limited time. If the reaction is limited to 30 minutes, distinct rolonies can be formed. The rolonies are then bound to a surface.

Figure 21:
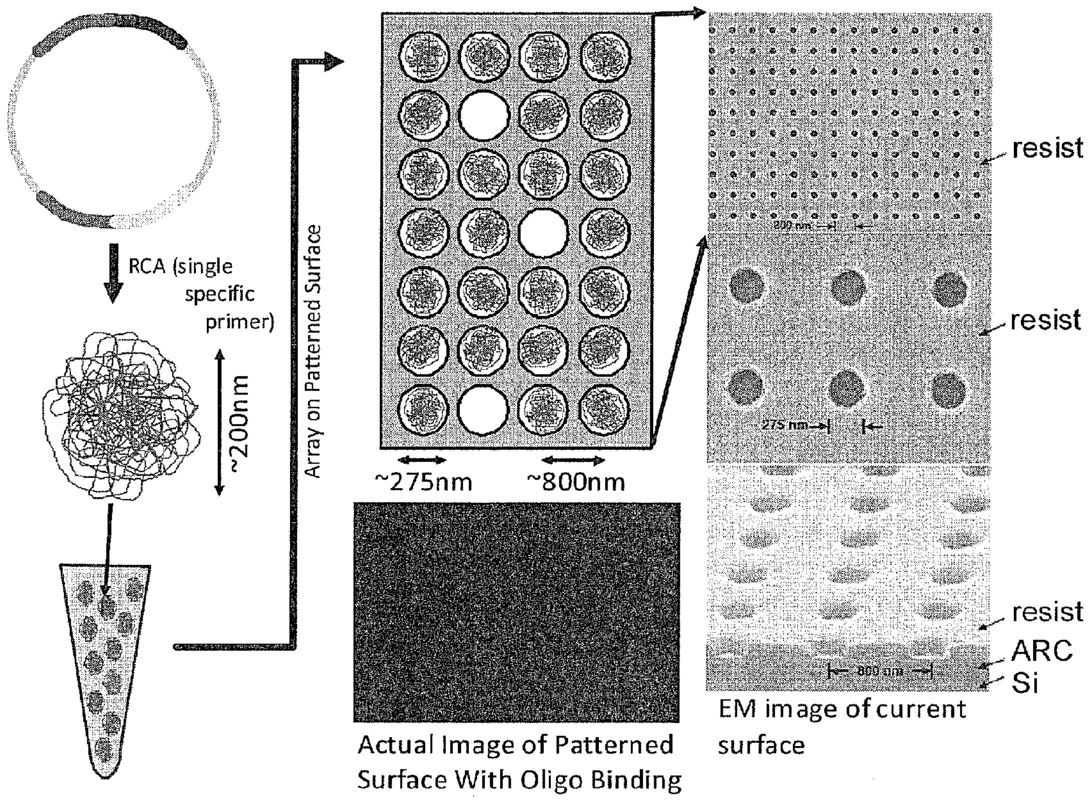

FIG. 21. A schematic diagram illustrating one approach for patterning rolonies on a surface.

Figure 22:
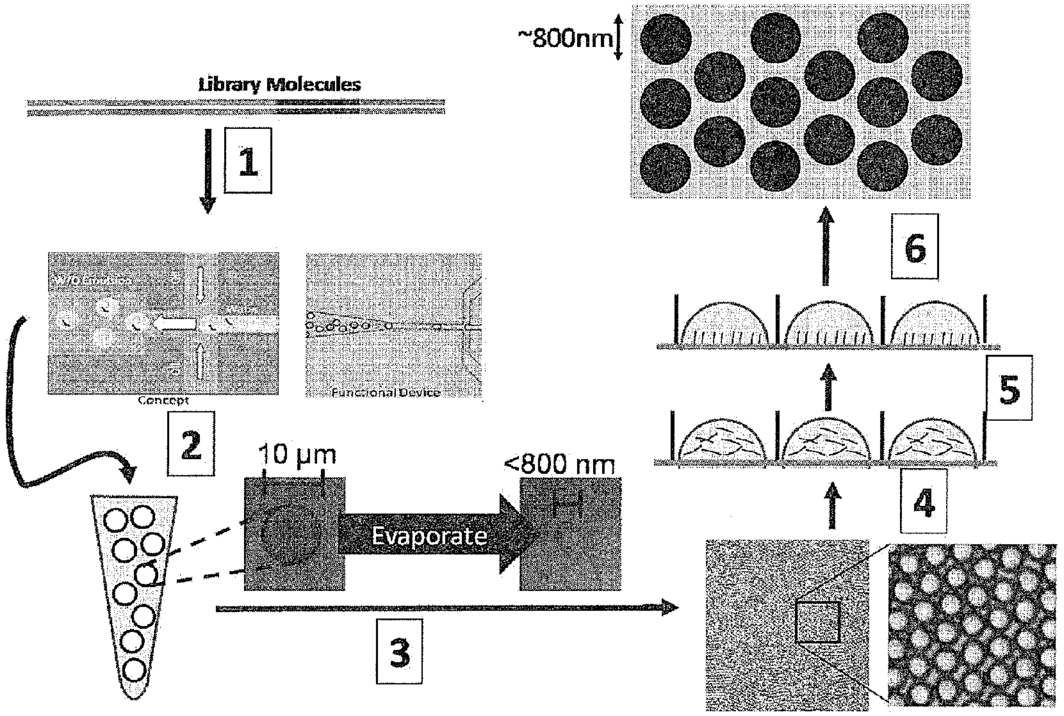

FIG. 22. A schematic diagram illustrating emulsion droplet deposition. (1) Mono-dispersed emulsion microdroplets of PCR mixed with a single library molecules (10 μm in diameter) are generated using a microfluidic device and Poisson loading of DNA into droplets. (2) The emulsion is thermal cycled. (3) The drops are mono-dispersed at ~10 μm. To generate small drops for arraying, we evaporate water through oil continuous phase to shrink droplets to <1 μm diameter. (4) The emulsion droplets are dispersed in a monolayer on a patterned glass surface that is functionalized to bind the amplified DNA fragments. (5) The emulsion is broken and the droplet contents are selectively deposited to specific locations on the glass surface. Biotinylated DNA will bind to streptavidin-coated surface. (6) Finally, the surface is washed to remove emulsion and DNA remains bound in a high density pattern.

Figure 23:
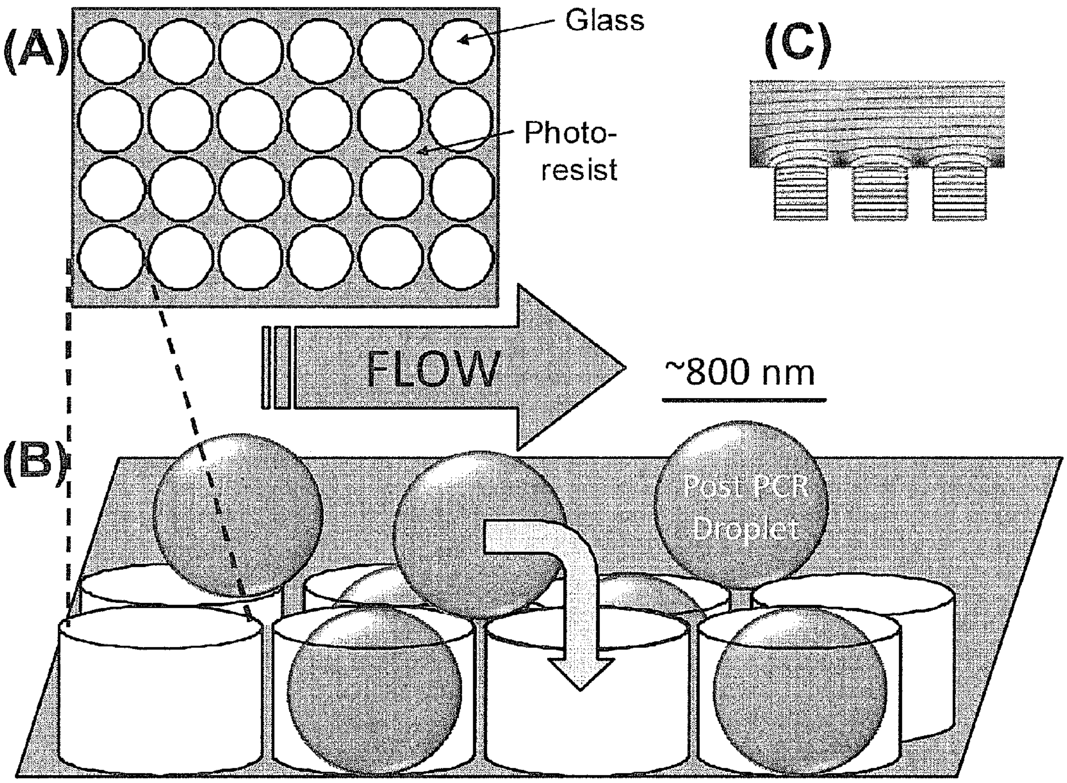

FIG. 23. A schematic diagram illustrating patterned deposition of PCR droplets. (A) Patterned surface. (B) Loading of the patterned surface is by flow over the surface and dielectrophoresis responsible for well loading. (C) Comsol predicted electric field near the well. The large change in potential in the area around the wells indicates a droplet near the well may be pulled in by dielectrophoresis.

Figure 24:
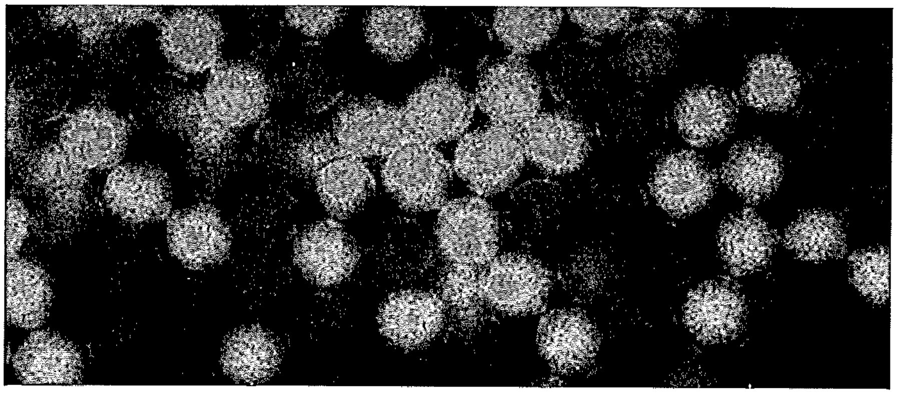

FIG. 24. The results of a molecular beacon assay identifying drops with DNA.

Figure 25:
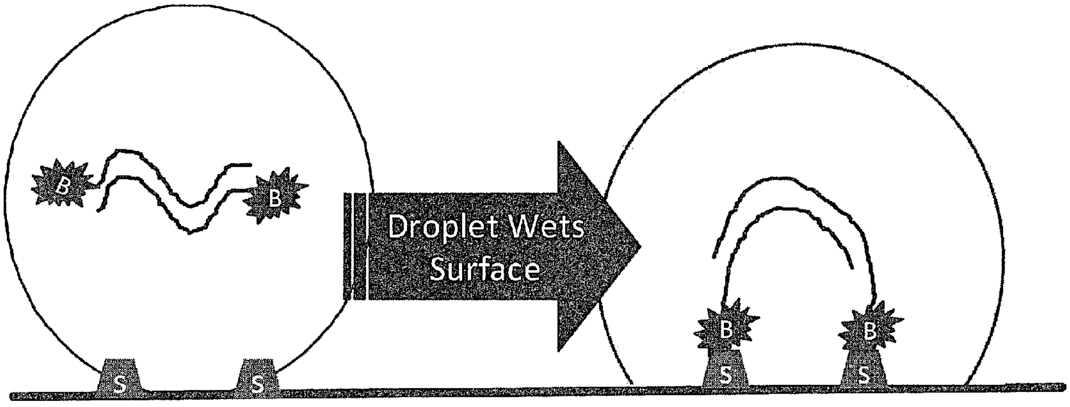

FIG. 25. A schematic diagram illustrating biotinylated amplicons within a droplet compartment will bind streptavidin on the glass surface upon wetting of the droplet. Both the forward and reverse primers can be biotinylated which will lead to the double stranded DNA forming a bridged morphology.

Figure 26:
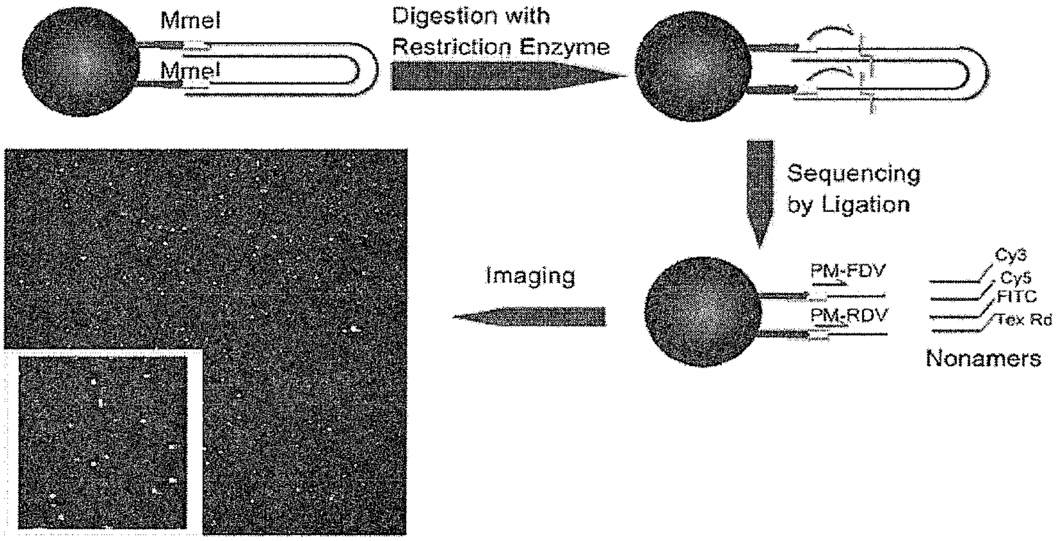

FIG. 26. A schematic diagram illustrating DPePCR. Since both strands are attached to the bead it is not possible to hybridize an anchor primer or perform SBL. Therefore, we have designed the DPePCR primers to have an MmeI site so we can digest the beads and release the complementary DNA from the regions we want to sequence. We have successfully sequenced DNA from both anchor primer sites (PM-FDV and PM-RDV in the figure). The image is an actual position we sequenced from a DPePCR.

FIG. 27. Simulations for Chromosome 1. $10^6$ random 300+/−100 base tags were generated from Chromosome 1. 7-13 bases from each end were used to determine the uniqueness of the map back to the chromosome. The % tags that mapped 1-10 times is shown. For example, in this figure, 26 bases means 13 were sequenced from each end. The numbers are essentially the same if the paired reads are 16 and 10, etc. The simulations were performed with balanced reads to simplify the preliminary analysis.

Figure 28:
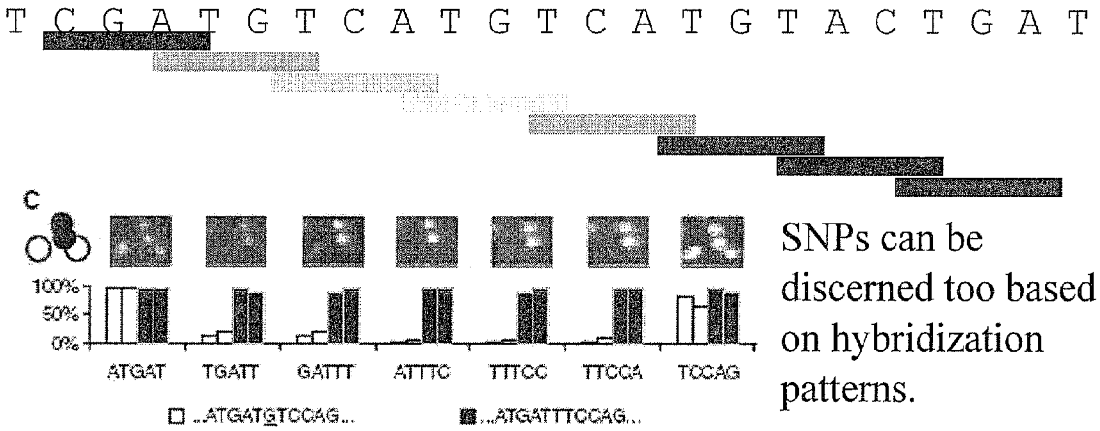

FIG. 28. A schematic diagram illustrating the SBH approach. Based on positive and negative signals for hybridization, the sequence (SEQ ID NO:36) can be reassembled. SBH results may be used to identify sequence variants.

Figure 29:
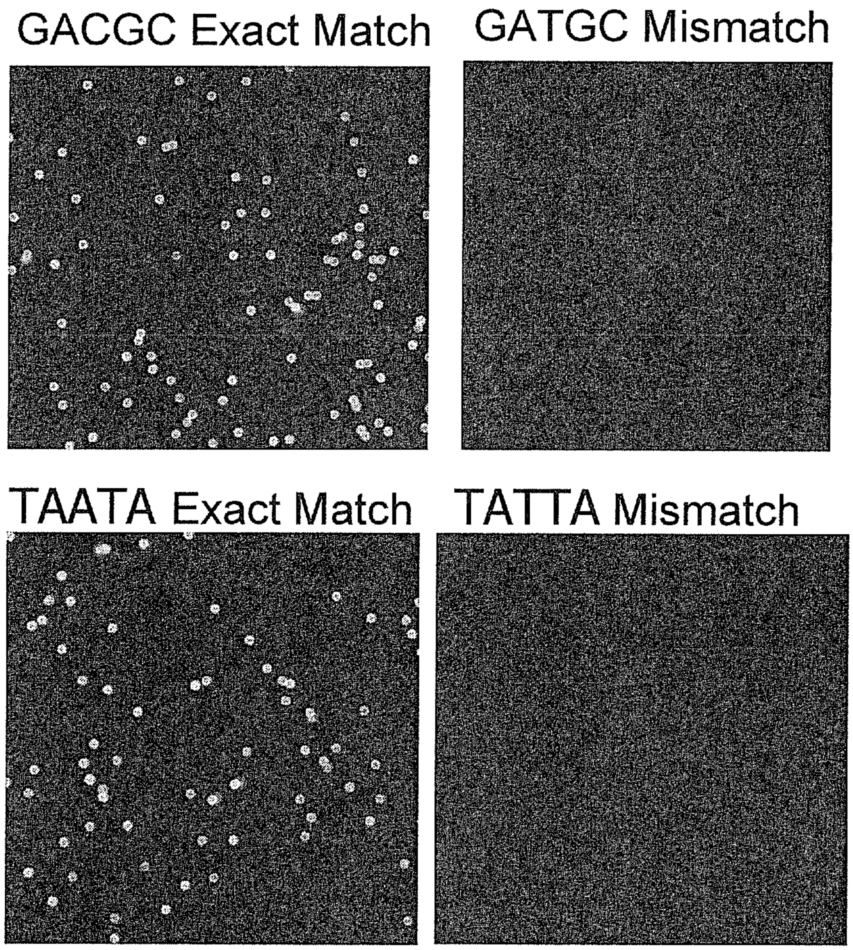

FIG. 29. Preliminary Probe Test Data. Data generated using four probes to probe SEQ ID NO:37 are shown: two probes provide perfect matches and two probes possess a single base mismatch. Also, two of the probes have high GC content and two have high AT content. We have been able to successfully identify single mismatches using different buffers. The GC rich probe was annealed in 6×SSPE at RT. The AT probe was annealed in 1×SSPE with 20 mM $Mg^{++}$ at RT. Both these primers are 9-mers (defined 5-mer with two random bases on each end. The 5-mer region was made up of all LNA bases).

Figure 30:
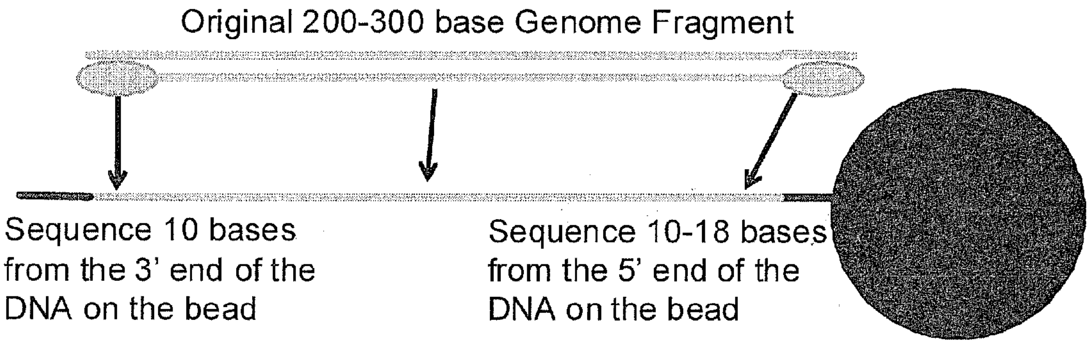

FIG. 30. A schematic diagram illustrating combined SBH+SBL.

Figure 31:
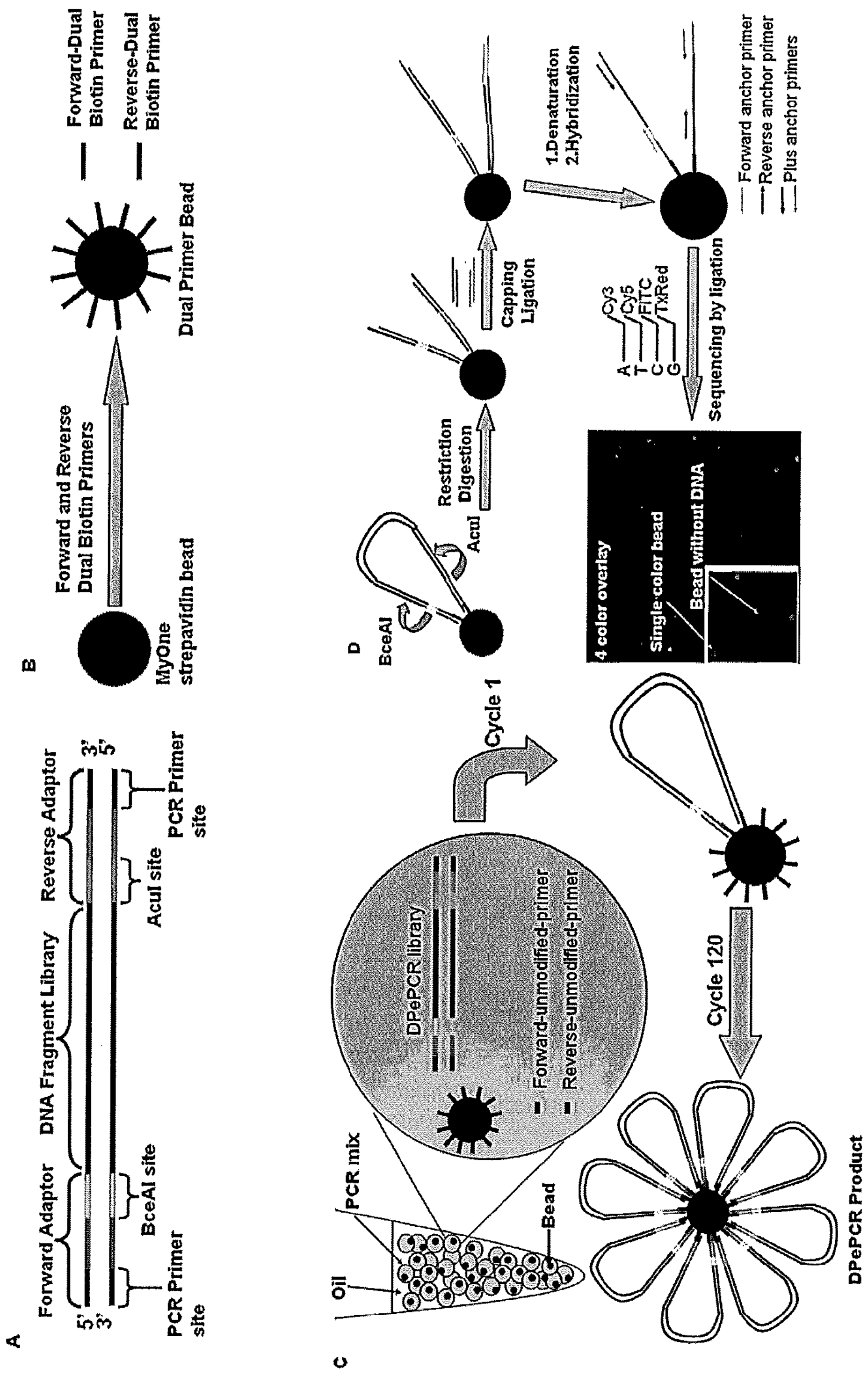

FIG. 31. A schematic diagram illustrating Dual Primer emulsion PCR. (A) The DPePCR library: 70-130 base pair DNA fragments were ligated to forward and reverse adaptors: FDV2-BceAI-Primer-F/R and RDV2-AcuI-Pimer-FIR. Restriction enzymes sites recognition were designed for BceAI and AcuI at the ends of the two primers for digestion of the DPePCR product. (B) Dual Primer beads: equal amount of FDV2-dualbiotin and RDV2-dualbiotin were attached to MyOne strepavidin beads. (C) Dual primer beads, diluted DNA fragment, ePCR reagents and two both free primers were mixed with silicone oil phase. The goal is for each microdroplet to contain a single bead, single DNA molecule, and enough PCR reagents for clonal amplified. After 120 cycles, amplified DNA bridges form. (D) Digestion and sequencing of the DPePCR beads: After the emulsion amplification, the DPePCR beads are digested with BceAI and AcuI. The digestion will leave 13 bases on the forward (BceAI) strand and 15 bases on the reverse (AcuI) strand of fragment DNA for sequencing. Specific anchor primers are hybridized at the end of the forward and reverse strands (individually), following by sequencing by ligation.

Figure 32:
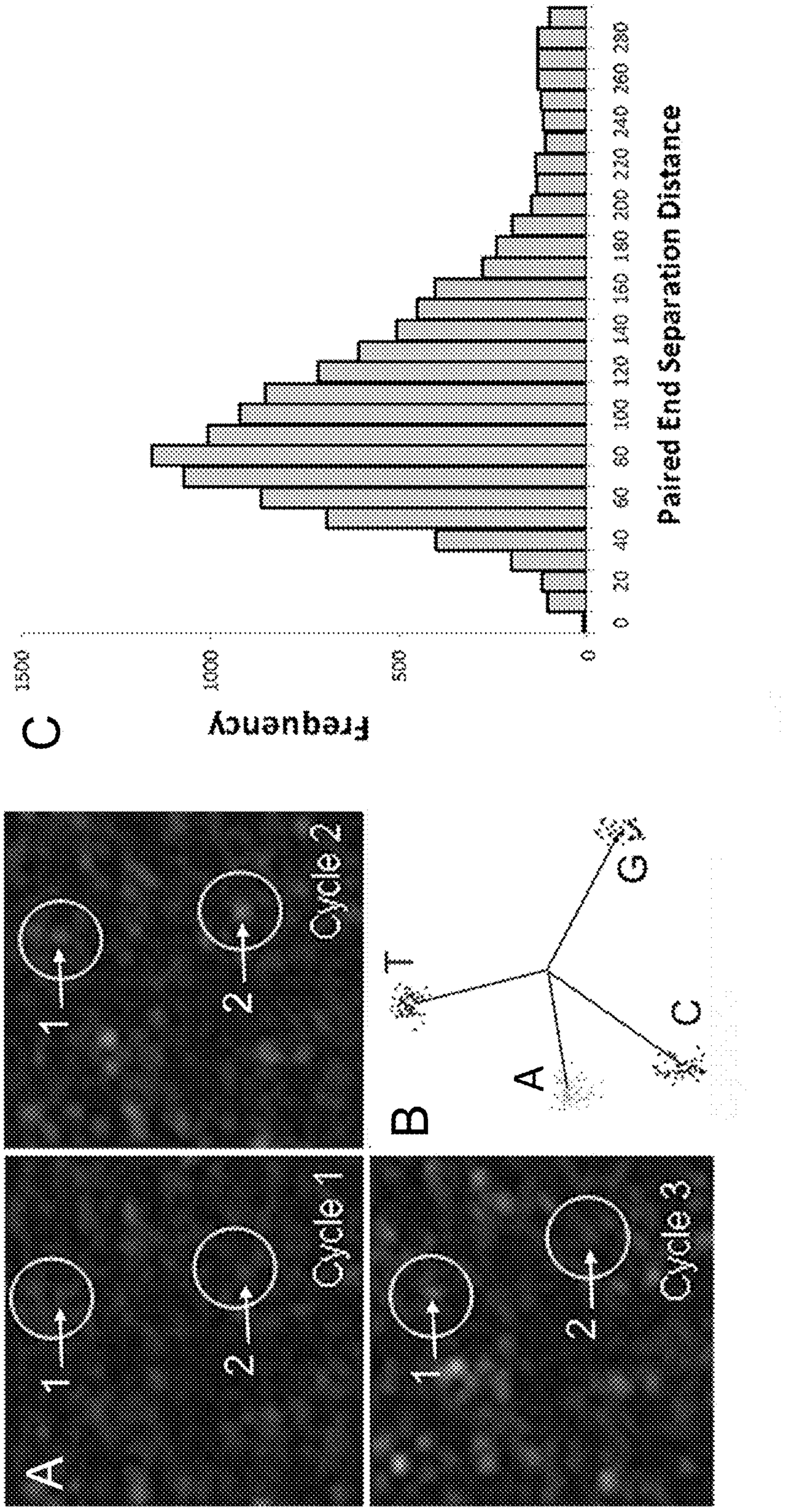

FIG. 32. Validation of Polonator DNA sequencing image. (A) The DPePCR beads were sequenced using sequencing by ligation. Green, red and blue beads relate to A, T and C, respectively, in the image shown. Note, the images are displayed in RGB for visualization, and the forth base is present, just not shown. For example, the sequence from bead 1 is CTT; bead 2 is TAC from the three cycles shown. (B) The tetrahedral plot is used for the base calling. Each dot on the plot corresponds to a single bead at one cycle in the sequencing. The normalized fluorescent intensity in all four channels is plotted in 4D and displayed here in a 3D plot. The base is called by the highest intensity value. The quality each call is defined as the distance from each bead to the centroid of the beads that have been called the same base. Since each of the beads is a clonal amplicon, the data points are clustered into 4 groups. The top 50% of the data from a single frame is shown in the figure. (C) The histogram shows the average separation in the genome is about 100 bases, of a random sampling of ~20,000 reads that mapped uniquely to the *Streptococcus pyogenes* genome (AE014074). Thus, the beads are clonal amplicons of ~100 bp fragments from the *S. pyogenes* genome.

DETAILED DESCRIPTION OF ILLUSTRATIVE EMBODIMENTS

Herein we describe novel approaches to Polony Sequencing Technology. Several approaches are described that can reduce the time and cost associated with, for example, sequencing the entire genome of an organism such as, for example, a human. Polony sequencing technology as described can provide cost-effective personalized genomic sequencing and can contribute toward personalized medicine.

We describe ultra-high throughput polony genome sequencing that can permit, for example, generating raw data to re-sequencing the human genome in about one week (including library prep and sequencing) at a reasonable cost. The methods described herein include one or more of the following: (1) increasing polony sequencing read length, (2) improving library construction and emulsions protocols, (3) increasing bead density and/or moving to alternative clonal amplication strategies (other than emulsion PCR or ePCR), and (4) extending software capabilities to allow SNP calls from our new sequencing raw data.

Thus, in one aspect, the invention relates to sequencing a complex mixture of nucleotide fragments (e.g., genome fragments), by a two-step sequencing protocol. First, at least five bases of the end of a fragment are sequenced, thereby identifying the fragment as one of a limited number of possible fragments. Second, at least a apportion of the remainder of the fragment is sequenced using Sequencing-by-Hybridization.

In another aspect, the invention relates to methods of increasing the read length of polony sequencing methods. If the read length is improved, more sequence is generated on a per run basis, thus decreasing costs associated with upstream steps, such as emulsion PCR. Additionally, increasing the read length improves the data quality and makes data analysis more efficient. We describe herein strategies to improve the read length: (1) sequencing-by-ligation read length improvements by cyclic ligation (Example 1), and (2) altered library prep and emulsion techniques that allows more reads per bead (Example 2 and Example 4).

In another aspect, the invention relates to methods of improving the construction of libraries for polony sequencing methods. Constructing sequencing libraries is often a rate limiting step for complex mate paired libraries due to the cost and/or time required to construct the library. We describe herein below the construction of sequencing libraries using strategies that can make the library preparation easier and/or less costly (Example 2).

In another aspect, the invention relates to methods of increasing bead density and/or moving to alternate clonal amplication strategies for polony sequencing methods. Increased bead density, or otherwise increasing the density of amplicons for sequencing, is one effective approach for decreasing the cost associated with genome sequencing. Namely, without any changes in chemistry, if 10× more beads are sequenced, then 10× more data is generated. We describe herein strategies to increase bead density including, for example, developing an enrichment strategy to select beads that contain DNA (Example 2), developing a rolling circle amplification strategy to replace the beads (Example 2), and developing a bead-less emulsion strategy where amplified DNA is directly deposited on a surface and sequenced, which we call Emulsion Array Elements (Example 2).

In yet another aspect, the invention relates to improvements in software that improve the analysis of the raw data obtained from polony sequencing methods.

As used herein, the term "and/or" means one or all of the listed elements or a combination of any two or more of the listed elements. The teams "comprises" and variations thereof do not have a limiting meaning where these terms appear in the description and claims. Unless otherwise specified, "a," "an," "the," and "at least one" are used interchangeably and mean one or more than one. Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

There are a number of innovative "next-generation" ultra-high-throughput sequencing technologies under development[4-6] (i.e. Illumina/Solex, SOLiD, Roche/454, Pacbio, Complete Genomics, IBS, etc.). Issues associated with high-throughput sequencing technology include: (a) cost per raw base, (b) throughput per instrument, (c) accuracy per raw base, and (d) read-length per independent read.

Polony sequencing offers one or more of the following advantages over other ultra-high-throughput sequencing technologies: (1) Polony sequencing is cost effective. It may be reasonable to sequence the entire genome of an individual for $1000 or less using polony sequencing technology. (2) Polony sequencing is versatile and adaptable. (3) Instrumentation for polony sequencing is commercially available and users can easily adapt this system for many novel applications. This adaptability is not always possible with other commercially available systems. Polony sequencing technology can be largely "off-the-shell" and as widely accessible as other methods. (4) For many labs, a polony sequencing system is much more affordable than higher priced ultra-high-throughput sequencing systems.

Polony sequencing method can generate raw sequence with an error rate of better than 99.7% accuracy, which is on par with Sanger sequencing. Thus, 3× coverage of each base can yield an error rate of 1/100,000 bp. Ensuring a minimum 3× coverage of >95% of bases of the human genome requires approximately 6.5× coverage, or approximately 40 billion raw bases of sequence. This goal can be met by the technology described herein.

In the human genome, there are a substantial number of recently duplicated sequences, therefore, only approximately 73% of 20 bp genomic "reads" can be assigned to a single unique location human genome. It has been estimated that sequencing reads of 60 bases will be required for >95% unique assignments and >99% uniqueness will require >200 bp reads. With 26 bp mate paired reads—the standard polony sequencing read length—unique mapping of at least 80% of the reads is obtainable. Based on our simulations, if 80% of the reads uniquely map to the chromosome, 83-85% sequence coverage is obtainable. Based on our simulations, 96% sequence coverage is obtainable using 36 bp continuous reads and the improvements in read length described herein (Example 1). Thus, sequencing the human genome with very short reads is achievable.

Figure 1:
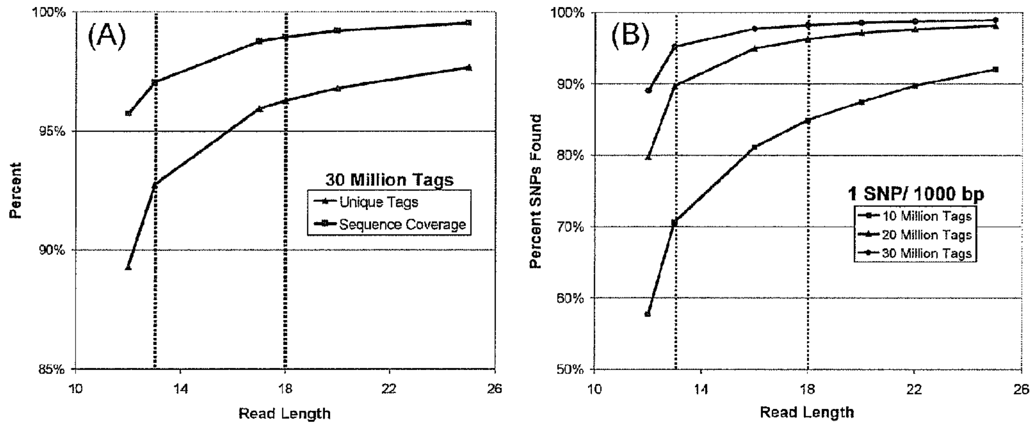
FIG. 1: (A): This figure shows the percent of sequenced tags that are unique as a function of the read length of a single tag. We sequence mate pairs, so the total sequence obtained is 2× the read length. We used Chromosome 6 for these simulations. The figure also shows percent of sequence covered. This number is always slightly higher than the percent of tags that uniquely map. (B) We utilize Chromosome 6 and randomly insert SNPs at an overall rate of 1/1000 bp. We then used simulated reads to determine the percent of SNPs that were accurately identified. The results are shown on this figure as a function of read length and the number of tags sequenced. In both figures, the traditional polony read length (13 bp) is highlighted by a dotted line. Additionally, a 18 bp read is also highlighted with a dotted line.
Figure 3:
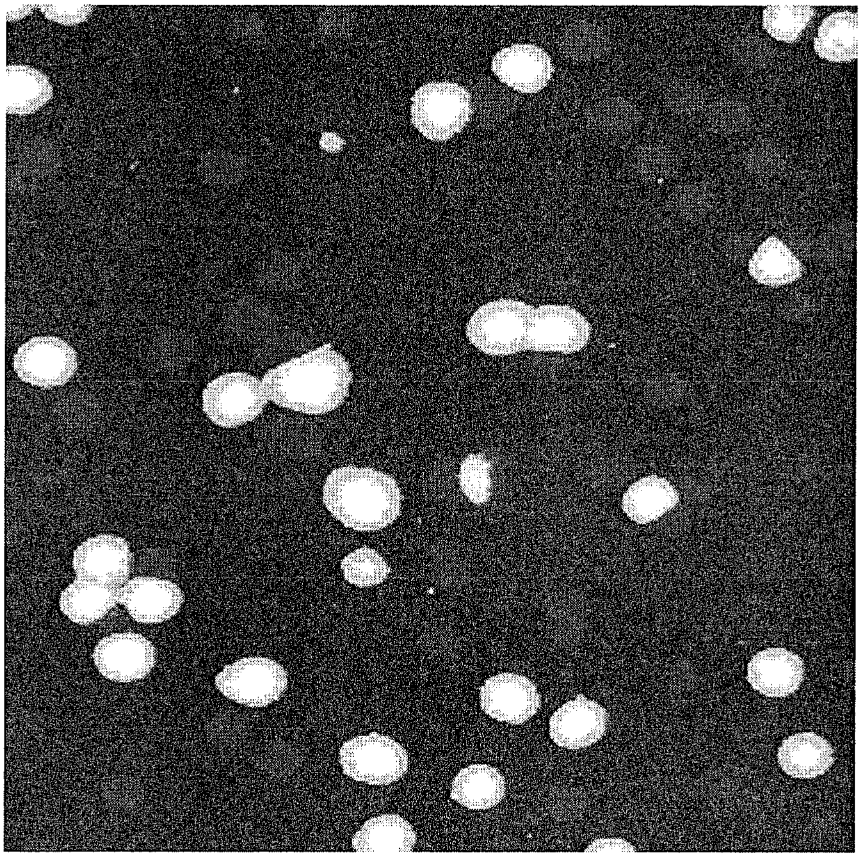
FIG. 3. Polony amplification of a DNA bar code that has been used to study the affect of mutations in the tetramerization region of p53.

Human genome sequencing with short reads benefits from mate pair or paired end sequencing. FIG. 1 shows the theoretical maximum coverage as a function of the mate pair separation distance. FIG. 1 indicates that, for example, 36 bases of paired sequencing (18 bases at two paired sites) is more valuable than 36 continuous bases. Therefore, the paired sequencing inherent to polony sequencing is highly valuable.

We have performed extensive simulations to determine the coverage obtained from our sequencing reads. These simulations have been used to optimize the re-sequencing parameters, such as mate pair separation distance, total number of bases required, etc. Additionally, we have used these simulations to determine the number of reads and the read length required to obtain a defined coverage or identify a defined number of SNPs. Also, we have developed highly optimized code that provides analytical speed. We have extended our code to run in 64-bit mode on a super computer at the University of New Mexico High Performance Computing Center that has 256 GB of RAM. At this time we have performed a number of simulations on the entire genome, which allow us to extrapolate the simulation data to predict, generally, whole genome re-sequencing capabilities using the methods described herein.

Classic Polony Sequencing

Classically, a polony (or PCR colony) is a colony of DNA that is amplified from a single nucleic acid molecule within an acrylamide gel such that diffusion of amplicons is spatially restricted. One dilutes a library of DNA molecules into a mixture that contains PCR reagents and acrylamide monomer. A thin acrylamide gel (approximately 30 microns (μm)) is poured on a microscope slide, and amplification is then performed using standard PCR cycling conditions. If one begins with a library of nucleic acids such that a variable region is flanked by constant regions common to all molecules in the library, a single set of primers complementary to the constant regions can be used to universally amplify a diverse library. Amplification of a dilute mixture of single template molecules leads to the formation of distinct, spherical polonies. Thus, all molecules within a given polony are amplicons of the same single molecule, but molecules in two distinct polonies are amplicons of different single molecules. Over a million distinguishable polonies, each arising from a distinct single molecule, can be farmed and visualized on a single microscope slide.

In our protocols, one of the amplification primers includes a 5'-acrydite-modification. This primer is present when the acrylamide gel is first cast, such that it physically participates in polymerization and is covalently linked to the gel matrix. Consequently, after PCR, the same strand of every double-stranded amplicon is physically linked to the gel. Exposing the gel to denaturing conditions permits efficient removal of the unattached strand. As every copy of the remaining strand is physically attached to the gel matrix, we can perform a variety of biochemical reactions on the full set of amplified polonies in a highly parallel reaction. In the current faun of polony sequencing, the 'polony' is a DNA-coated bead rather than in situ amplified DNA and 26-30 bases can be sequence from $1.6 \times 10^9$ beads simultaneously. It may be possible to scale-up the sequencing to 36 continuous bases (and up to 90 bases) from $2.8 \times 10^9$ beads simultaneously and maybe as many at $10^{10}$ using methods described herein below.

BEAMing (Also Called Emulsion PCR or ePCR)

Figure 4:
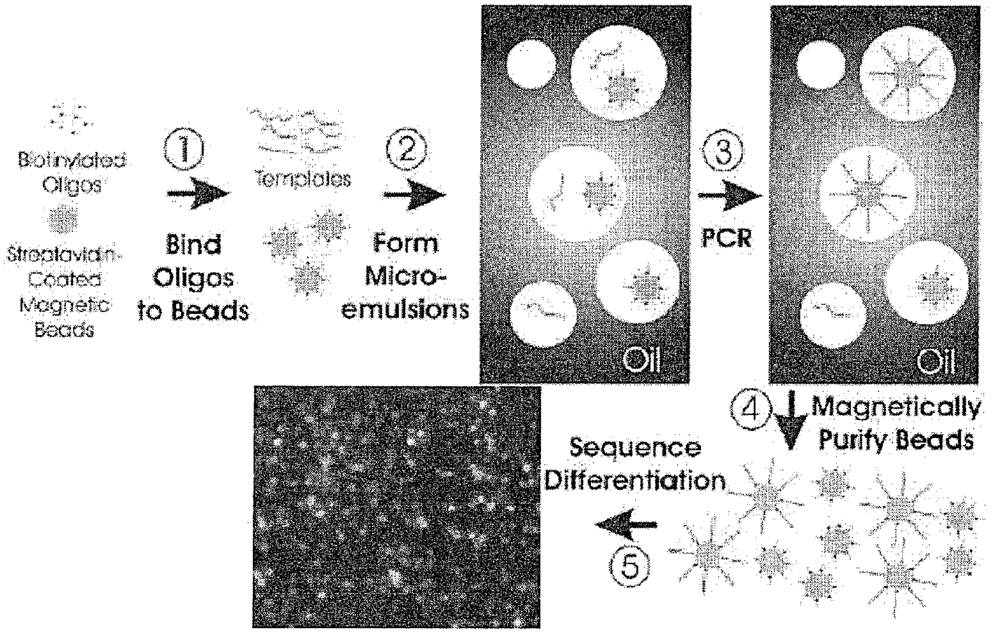
FIG. 4. A schematic diagram illustrating the steps of emulsion PCR.

In another approach, we use modified and optimized BEAMing protocols to create the DNA coated beads. High density polony bead arrays can be made using DNA-coated magnetic beads. BEAMing (also referred to herein as ePCR) is essentially a method for clonal implication of individual DNA molecules onto beads. BEAMing permits one to amplify single DNA molecules and simultaneously attach the PCR products to beads. BEAMing/ePCR allows one to coat a bead with identical DNA molecules. Furthermore, this technique has been developed to perform such an amplification in a poly-dispersed emulsion, thus allowing one to simultaneously coat $>10^7$ beads with DNA. BEAMing/ePCR is pictorially depicted in FIG. 4.

Polony Genome Sequencing

Polony sequencing for sequencing an entire bacterial genome was reported in 2005. In order to perform polony genome sequencing, one must first prepare a library for sequencing. Methods for preparing libraries are described (e.g., Shendure, J. et al. Accurate multiplex polony sequencing of an evolved bacterial genome. *Science* 309, 1728-32 (2005)) and we describe improved methods for library preparation herein. In traditional polony sequencing, the reads are short, seven bases in the 3'→5' direction and six bases in the 5'→3' direction. Therefore, the libraries are constructed so as to have two mate paired tags that can be sequenced from both directions, thus providing 26 bases per bead. Because of the extremely short reads, polony sequencing a fragment library has not been feasible, which is unfortunate because preparing a mate paired library is much more difficult.

Figure 6:
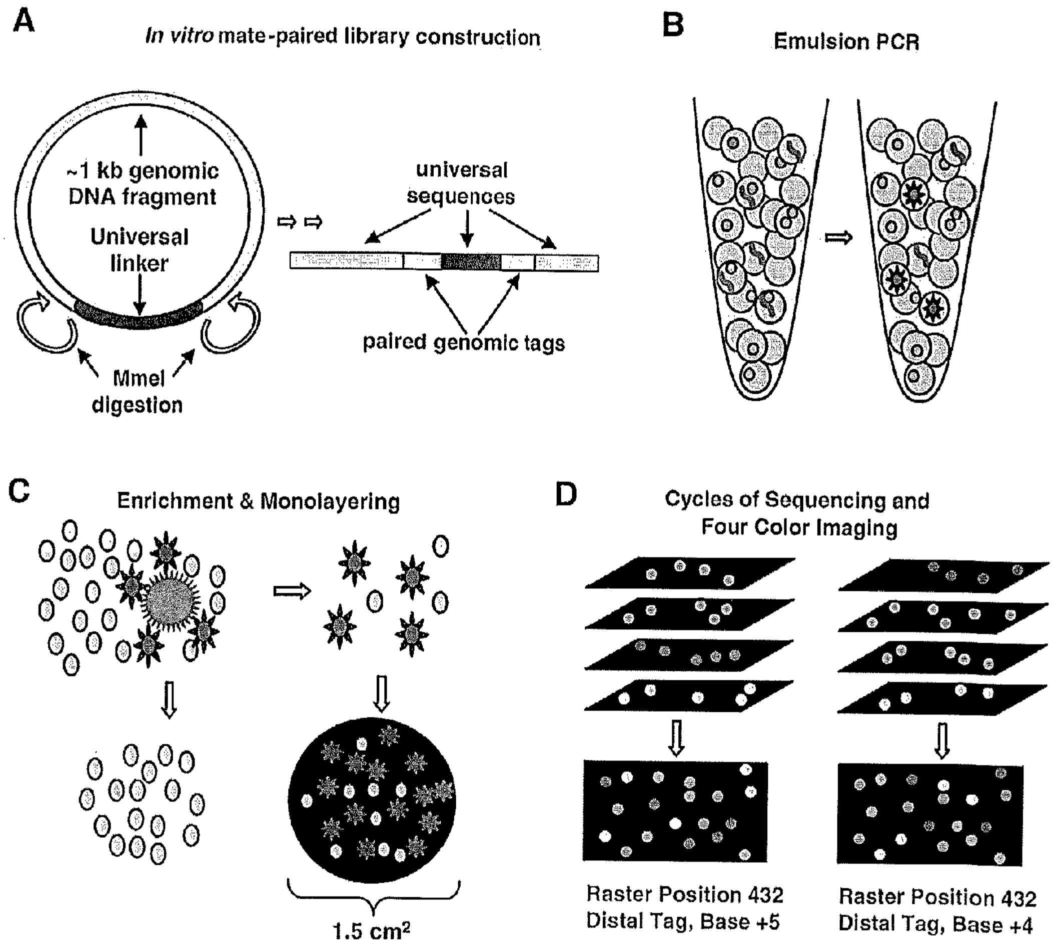
FIG. 6. PRIOR ART: schematic diagram illustrating the preparation of a polony genome sequencing library. (Published as FIG. 1 in Shendure et al., September 2005 *Science* 309:1728-1732.)

Original Library Prep. The library production begins with the isolation of genomic DNA and shearing the DNA to approximately 1 kb (or appropriately sized) fragments. These 1 kb fragments are isolated and circularized as shown in FIG. 6 with an adaptor primer (T30). The T30 primer includes the sequencing primer sites and MmeI type IIs restriction enzyme sites. The circularized library is amplified by hyperbranched rolling circle amplification (RCA). Next, the library is digested with MmeI, which releases a 70 bp fragment with T30 flanked by two 19 bp genomic tags separated in the genome by approximately 1 kb. The ends of the 70 bp fragments are ligated to sequencing/PCR primers, resulting in a 134 bp fragment, which is loaded onto beads by ePCR. Finally, these clonal beads are immobilized in a flowcell for sequencing.

Figure 5:
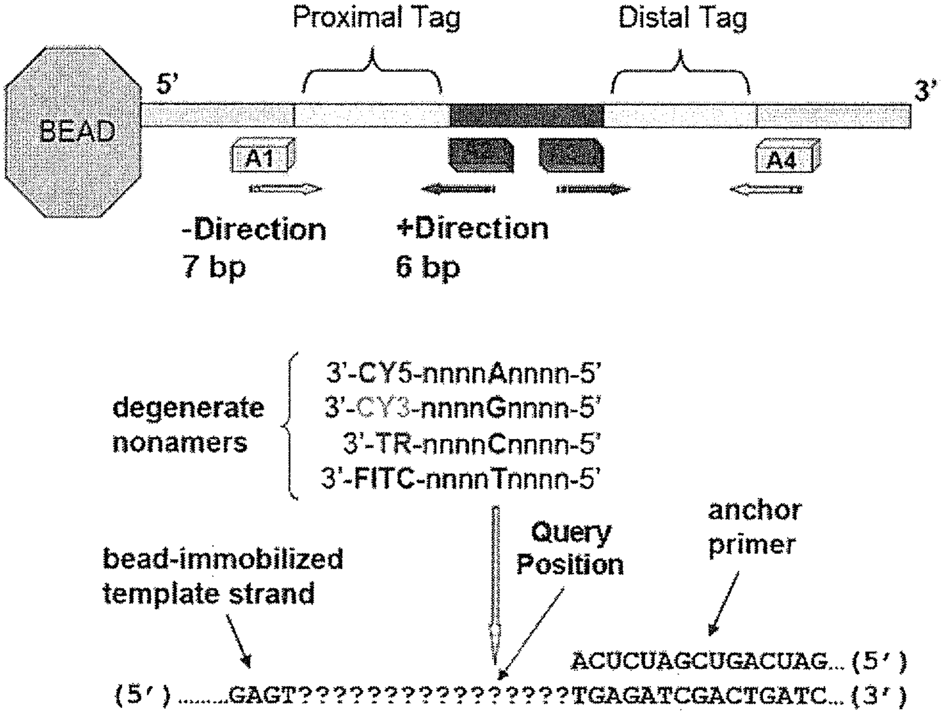
FIG. 5. A schematic diagram illustrating ligation sequencing of an exemplary bead-immobilized template DNA strand (SEQ ID NO:32) using an anchor primer (SEQ ID NO:31).
Figure 7:
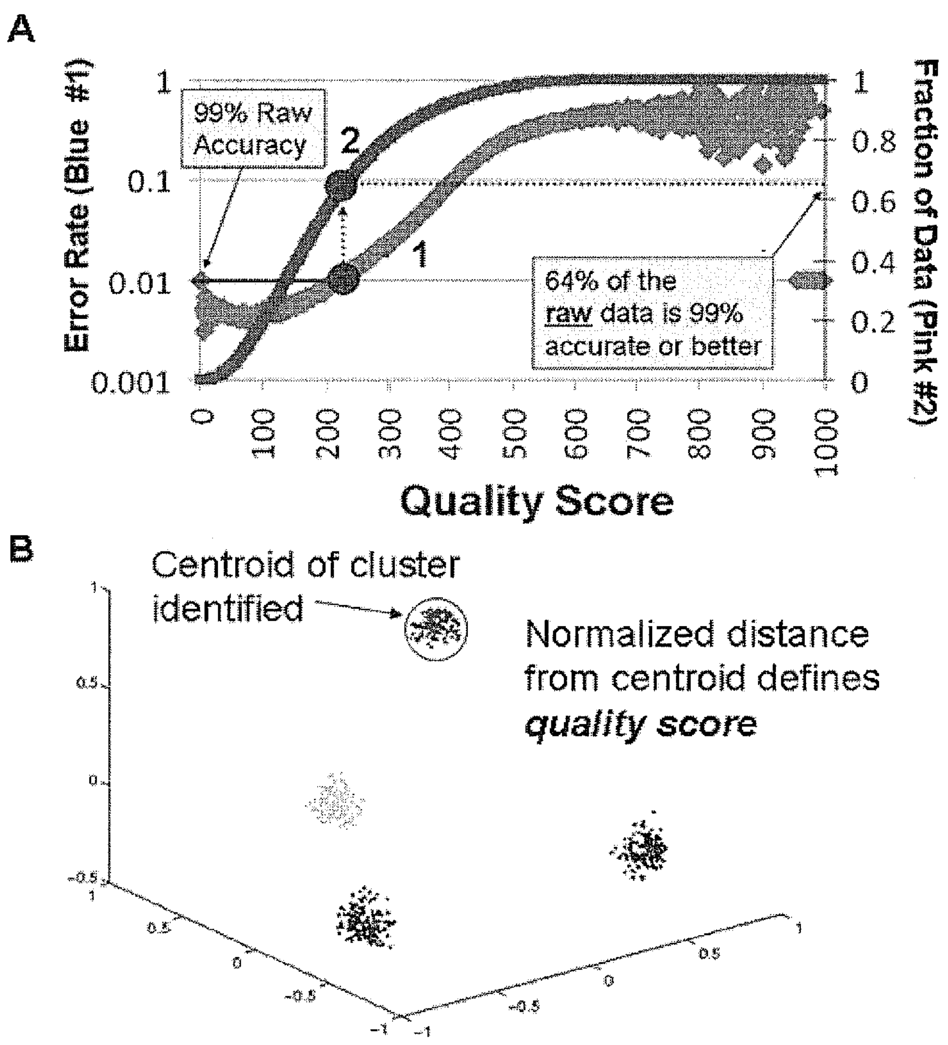
FIG. 7. (A) Curve #1 is the mapping between the quality score (defined in (B)) and the raw accuracy of the read. Curve #2 shows the fraction of data at a given quality score or better. For example, the quality score of 230 translates to 99% accurate and 64% of the data has a quality score of 230 or better. The accuracy was calculated by sequencing 60 Group A *Streptococcus* (GAS) genomes. (B) The quality score for each base is calculated by measuring the fluorescent intensity from the bead in all four channels, plotting in four dimensions. The centroid of all beads defined as each base is determined and the normalized distance to the centroid is defined as the quality score for each base.
Figure 8:
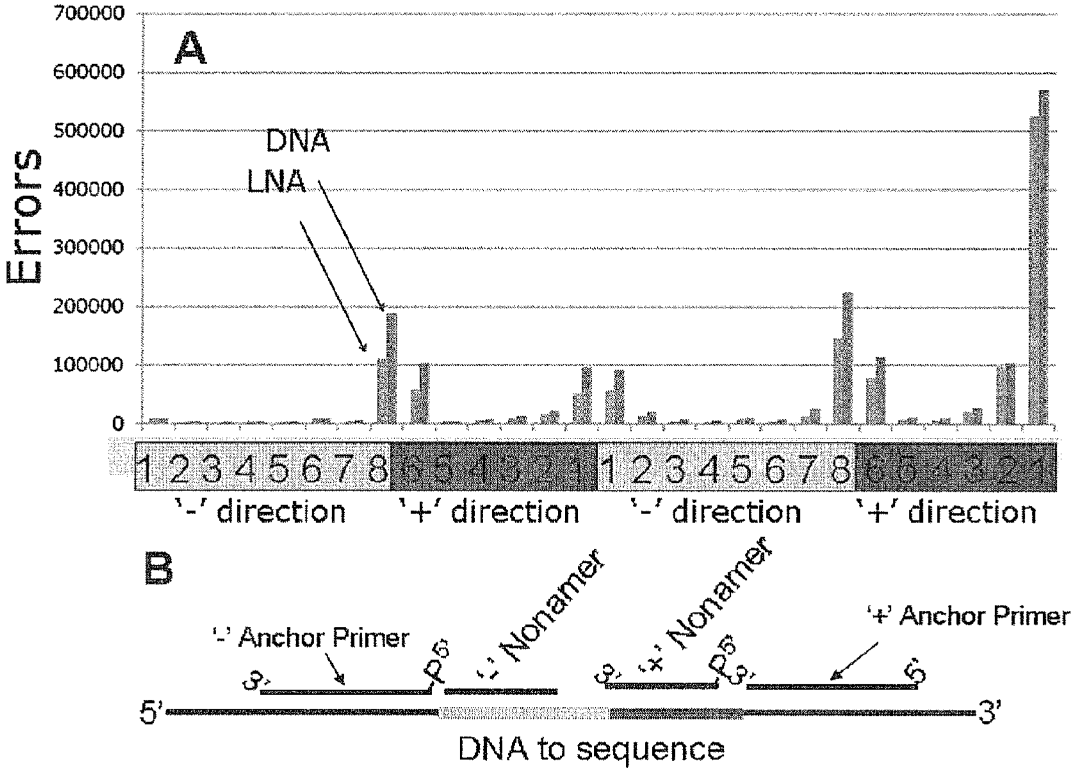
FIG. 8. (A) Error rate as a function of the position in the read. The error rate increases as the sequence base is further away from the ligation point. Also, error rate increases with "+" direction sequencing late in the run due to background buildup. (B) The definition of '+' and '−' direction sequencing. '+' direction sequencing is the same direction as polymerase based SBS chemistry.
Figure 9:
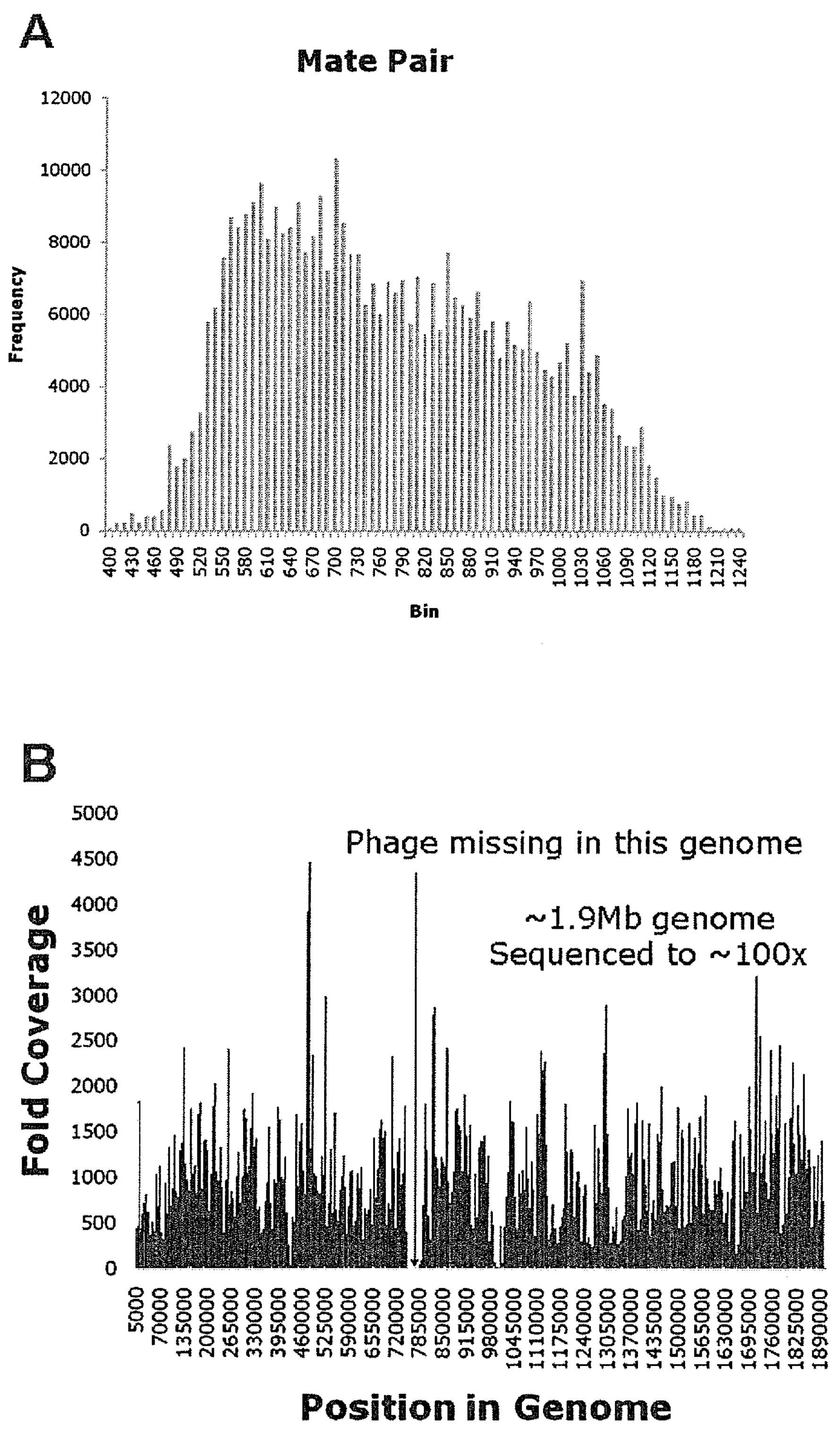
FIG. 9. (A) Mate pair separation distribution in one of our Group A *Streptococcus* libraries. (B) Genome coverage from our libraries.
Figure 10:
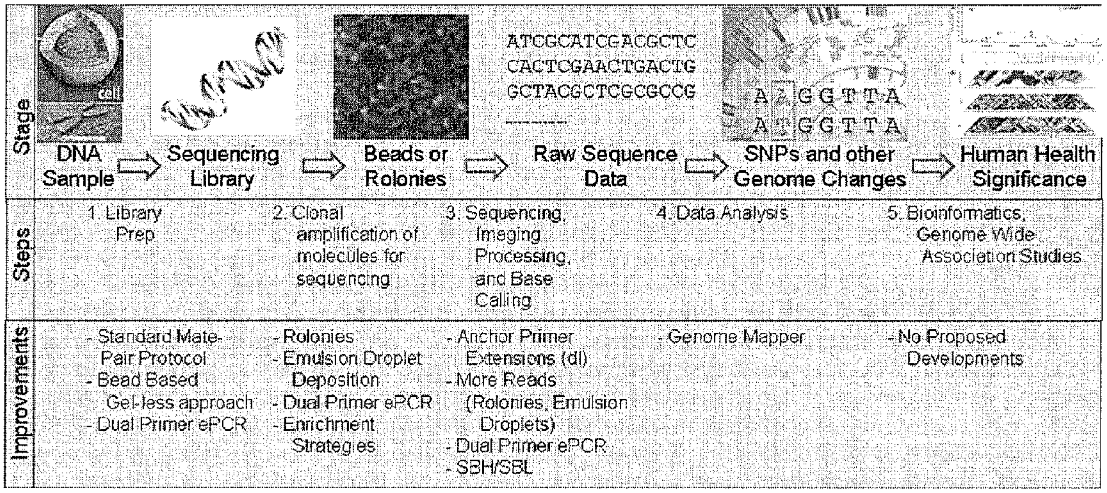
FIG. 10. A table summarizing steps for genome sequencing. Stages of the process are delineated in the top row, where a DNA sample that possesses the exemplary nucleic acid sequence SEQ ID NO:33 is processed all the way through sequencing and the identification of SNPs, etc. The steps indicated in the middle row identify the procedures preformed to move from stage to stage. The bottom row identifies certain features described herein.
Figure 12:
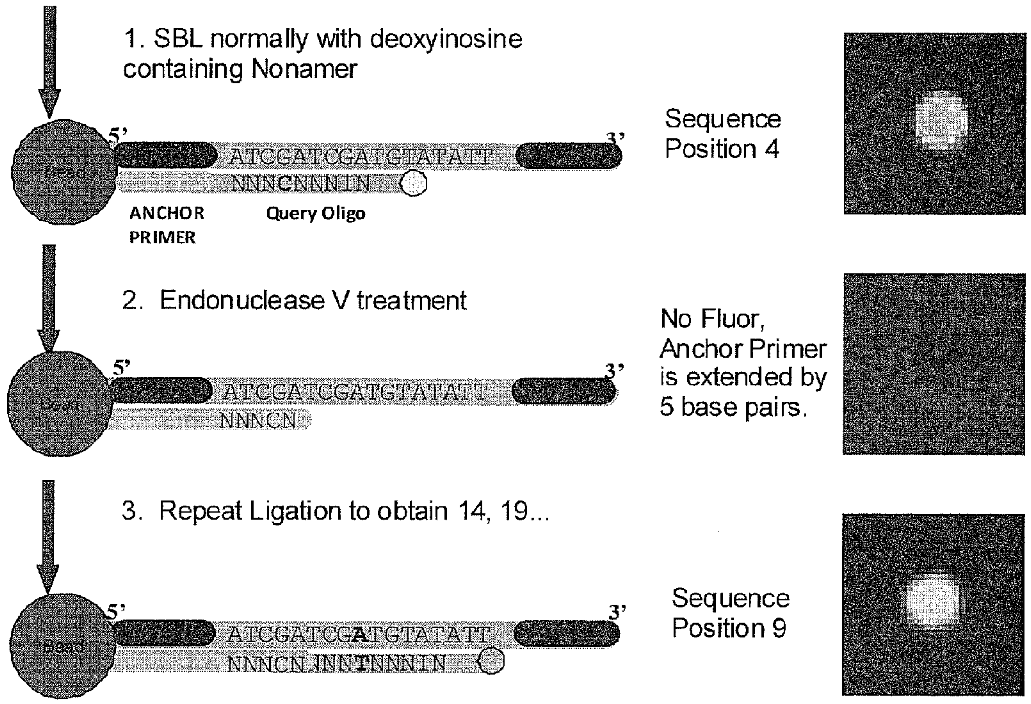
FIG. 12. A schematic diagram illustrating cyclic sequencing by ligation. By utilizing a query primer (SEQ ID NO:35) that contains a deoxyinosine, template DNA (SEQ ID NO:34)

Sequencing. The beads are sequenced by repeated rounds of annealing an anchor (sequencing) primer and ligation of degenerate nonamers (9-mers or Query Primers) to the anchor primer. The nonamers have a single fixed base that is identified with a fluorescent dye (FIG. 5). We have completed many bacterial sequencing runs (see raw data in FIGS. 7 and 8). The analysis of a recent sequencing run of an evolved *E. coli* has revealed 160 mutations in a strain that was selected for resistance to ionizing radiation. The raw accuracy of 64% of the data has been 99% accurate or better and 35% of the data has had a raw accuracy of 99.5% or better (See FIG. 5). Since we have an accuracy call for every base we are able to make final SNP calls with a defined probability.

Increasing Read Length

We have attempted a number of approaches to extend the read length. Many of the approaches were initially encouraging, but failed in implementation. For example, we have tried incorporating RNA bases in the nonamer and cleaving with RNA shredder. This approach works for certain RNA bases, but others are not cleaved at all by any of the RNases we tried. We have succeeded extending the read length using Endonuclease V cleavage of deoxyinosine in the nonamer. In certain embodiments, we have sequenced at least 12 continuous bases such as, for example, at least 18 continuous bases or at least 36 continuous bases on beads in suspension.

One issue that exists when sequencing by ligation is that secondary structure can cause certain sequences to be unsequenceable. The issue has been at least partially reduced in traditional polony sequencing by annealing "blocking" primers during the sequencing. However, in sequencing a fragment library as described herein, long regions can contain sequences with secondary structure. To remedy this, one can use one or more of the following approaches. The temperature may be increased up to 45° C., DMSO (e.g., up to about 10%) may be added to the ligation buffer, other reagents (e.g., Betaine) may be added to the ligation buffer, and/or the $Mg^{++}$ concentration in the ligation buffer can be reduced.

Longer reads are important for a number of reasons. One can sequence more bases per run, which can reduce sequencing cost due by, for example, reducing upstream processing (e.g., ePCR) and reducing in other fixed costs (e.g., flowcell). Also, longer reads can increase the theoretical coverage of the genome. Mapping longer reads (a) makes it computationally easier for one to identify SNPs, (b) makes it easier for one to identify genome amplifications, deletions, or rearrangement, and (c) allows for more accurate mapping and more mappable sequence.

Library Construction

Researchers have focused intense efforts on developing next-generation sequencing technologies and analysis strategies while efforts to improve library production have lagged behind. Options for a sequencing library include, for example, fragment library (paired end or unidirectional) or mate paired library. In a mate pair library, the tags being sequenced are typically 1-5 kb apart, whereas in a paired end fragment library, the tags being sequenced are typically only 100-300 bp apart in a typical next generation sequencing project. Fragment libraries are simple to construct, and a number of next generation sequencing approaches sequence fragment libraries. However, sequencing mate pairs increases genome coverage assuming the same total number of bases sequenced. Ideally, the optimal resequencing strategy is to sequence both fragment library paired ends and mate paired libraries.

Sequencing fragment libraries (unidirectional and paired ends) can lead to reduced genome coverage relative to a mate pair library. However, fragment libraries are simple to construct and, therefore, permit construction of more complex libraries, which may be desirable in genome resequencing.

Polony sequencing using mate paired libraries has typically been difficult and provides poor library complexity. The SOLiD system (Applied Biosystems Inc., Foster City, Calif.) has a mate paired library protocol that is nearly identical to the original polony sequencing library protocol. While there are minor changes that slightly simplify the protocol, the ease of use, robustness, and library complexity using the SOLiD system is not significantly better than the original polony sequencing library protocol.

Preparing a mate paired library for next generation sequencing is a multi-step process. Eliminating polyacrylamide gel electrophoresis (PAGE) steps can decrease time and cost associated with creating a sequence library. A robust approach that completely eliminates PAGE purifications can increase the rate of library production and the quality of the final library. Eliminating gel purification steps can increase library complexity for two reasons. First, typically, approximately 50% of the DNA is lost during a PAGE gel purification step. Second, more amplification is typically required for gel purification in order to generate enough DNA to be visualized in a gel.

We have developed a bead based strategy for purifying the restriction digestion product fragment that eliminates the need for PAGE purification. Our approach can provide a higher quality library that existing methods (e.g., SOLiD and Illumina) due to increased circularization efficiency.

Moving to a gel-less library may be desirable and more efficient. However, the absence of a PAGE purification step also reduces the opportunity for feedback confirming successful steps. Therefore, one or more of the following quality control steps may be performed. First, rolling circle amplification (RCA) may be performed following ligation. This is not typically performed, but a small sample may be saved after the ligation of the hairpin adaptors and this quality control step may be performed if the library is unsuccessful to troubleshoot the problem (FIG. 14). Second, PCR may be performed following circularization. This quality control may be performed to verify circularization efficiency, library complexity, and estimate the unpaired fraction of the library due to concatamerization (FIG. 14). Third, a final PCR gel may be run to verify final product size. Fourth, a final library validation may be performed by cloning and sequencing 5-10 clones.

The library production protocol is shown in FIG. 13. This protocol can be sufficient to sequence a human genome. We have two human libraries prepared using this approach. Both libraries and been validated by Sanger sequencing clones from the library. The libraries appear to have sufficient complexity based on the quality control steps we have implemented and the limited amplification that library has undergone.

The protocol differs from the original protocol for producing a library in at least the circularization step. Our estimates from quantifications through the protocol indicate that the circularization is nearly 100% efficient, given that only 50% of the molecules can potentially circularize. Also, all clones we have sequenced are correctly, paired. In other words, the bimolecular circularization issue appears to be minimized by binding both ends of the DNA to the beads. Thus, bimolecular circularization is spatially impossible, hence ensuring unimolecular hybridization/circularization.

Library complexity can be assessed by sequencing. The appearance of duplicate tags should be minimized. For example, if one sequences $10\times10^6$ tags, one should ideally see very few duplicate tags (i.e., identical sequence for both tags). If the test library is a Group A *Streptococcus* bacterial genome, one will have a potential of $2\times10^6$ tags, each mate paired with another tag that is 700 bp-1300 bp away. Therefore, one has a potential for $1.2\times10^9$ different molecules loaded on the beads. To measure the library complexity, we can statistically determine if the number of duplicate tags follows the expected distribution.

The mate paired libraries described above may be constructed using a restriction enzyme that cuts remotely from its recognition sequence. As used herein, a restriction enzyme cuts remotely from its recognition site if its cuts any distance outside of the recognition site. Certain Type I, Type II, and Type III restriction enzymes are known to cut remotely from the recognition site. Exemplary restriction enzymes include, for example, MmeI, which cuts 18/20 bp away from its recognition site, AcuI, which cuts 14/16 bp away from its recognition site, BceAI, which cuts 12/14 bp away from its recognition site, FokI, which cuts 9/13 bp away from its recognition site, and EcoP15Im which cuts 25/27 bp away from its recognition site. This library strategy permits, therefore, tags of up 27 bases, depending upon the restriction enzyme that is used. It may be desirable, however, to extends reads beyond this length, so it may be desirable in some embodiments to extend the library prep described above to large insert mate pairs.

Thus, in some embodiments, one can prepare a library using a modified library prep procedure. At the circularization step, the double stranded DNA can be nicked on both sides. The mate pair tags may be generated by nick translation with DNA Polymerase I into the unknown sequence. A controlled nick translation that extends approximately 100 bases will essentially move the single strand nicks over approximately 100 bases. The process is shown in FIG. 15. The nick translation can be followed by T7 exonuclease which has 5'→3' exonuclease activity to increase the size of the nick and create a gap. Finally, S1 nuclease can be used to cut at the ssDNA and leave a DNA fragment with a central linker and two approximately 100 base mate paired tags. The DNA fragments can then be processed as all our other tags. The mate pair libraries can be sequenced using the Quad Primer PCR approach described below (Example 2).

Alternatively, or in addition, one can also construct fragment libraries using standard methods. Namely, one can fragment the DNA and attach primers to the fragment ends for ePCR and sequencing. The fragment libraries can be sequenced using the Dual Primer ePCR strategy described below (Example 2).

Increasing Bead Density and/or Alternate Clonal Amplication Strategies

One way to increase sequencing throughput and decrease the cost of sequencing an entire genome is to increase the number of beads or other entity being sequenced. In the current configuration one can sequence 800 million beads per flow. The system is designed for dual flowcell runs, so 1.6 billion beads per run is feasible. In a typical run, only about 50% of the beads will have DNA and about 50% of those beads will have clonal DNA. Therefore, we could anticipate 400 million beads generating sequence. In a typical sequencing run, we see that about 50% of our reads can be successfully mapped back to the genome. Thus, we typically obtain 200 million reads of 28-30 bases or about 6 billion bases per run.

The simplest approach for increasing the number of reads is by increasing the number of beads that have DNA. This can be done by bead enrichment. Bead enrichment can increase sequencing throughput to over 20 billion bases per run because one may be able to reduce—perhaps even eliminate—beads that lack DNA and/or the number of non-clonal beads. Furthermore, one may be able to increase the number of mappable reads by increasing read accuracy. Therefore, it may be possible to generated 30 billion bases per run at the current read length. With the proposed changes in Example 1 and Example 2, it may be possible to increase the read length to 60 (or more) bases/bead, thereby generating 60 billion mappable bases per run, which is sufficient for complete resequencing a human genome.

The density of the sequencing entities can be increased beyond bead enrichment by switching to a fundamentally different approach. Alternate approaches can possibly move beyond the density limit imposed by working with 1 μm beads. Furthermore, beadless methods can decrease the cost of sequencing because bead-based ePCR can be expensive and time consuming to perform.

One approach for eliminating beads is known as rolonies, or RCA (rolling circle amplification) colonies. Rolonies have been successfully used in a SBH genome sequencing strategy. However, the rolonies were generated in situ, on a surface and were randomly distributed on that surface. Instead, one can generate rolonies in solution and then place them on a surface. One can place the rolonies on a patterned surface at very high density (see FIG. 21). The patterned surface can be simply photoresist that is patterned using standard photolithograph equipment. In this way, one could obtain 3.2 billion rolonies per dual flowcell run. One can sequence rolonies made from mate pair libraries with standard polony sequencing ligation based sequencing. The rolony read length can influence the proper rolony library (e.g., a standard library with EcoP15I or approximately 100 bp mate pair library). Conservatively, one can sequence 24 bases from an EcoP15I library. Thus, when both mate pairs are sequenced, one can obtain 48 bases per rolony, or a total of over 150 Gbases, which can translate to over 75 mappable Gbases.

Emulsion Deposition

As an alternative to rolonies, PCR may be performed in an emulsion and the clonal PCR amplicons are directly deposited on a surface. The basic concept is illustrated in FIG. 22. This approach can produce dense DNA clonal arrays on a patterned surface.

Single-molecule DNA amplification can be performed in microdroplet emulsion reactors. Droplet-based microfluidics can facilitate the production of highly monodisperse microdroplet reactors at rates up to one kilohertz. Beadless loading of DNA molecule into the droplets can be achieved via dilution. The resulting droplets can be 10-15 μm and they can be collected from the microfluidic device in a microfuge tube and thermal cycled. The amplified droplets can then be shrunk to sub micron size and arrayed for ultrahigh density sequencing.

ePCR is typically performed using microdroplets 10-15 μm in diameter. This size is typically too large for a high density array of microdroplets, but it can produce efficient PCR amplification. A typical PCR primer concentration of 1 μM in a droplet reactor 10 μm in diameter (0.52 picoliters in volume) can produce a maximum of $3.15\times10^5$ double-stranded amplicons. Because volume, and thus number of amplicons possible at a given primer concentration, scales as the droplet radius cubed, droplets below 10 μm in diameter may not produce enough amplicons for sequencing by SBL or SBH. For example, a 1 μm droplet may only produce a maximum of 315 amplicons. However, to create a densely packed droplet array, it may be necessary to order droplets less than 1 μm in diameter. To circumvent this problem, one can first PCR amplify single molecules in droplets of at least 10 μm in diameter and subsequently shrink the droplets via evaporation of solvent through the oil continuous phase. We have previously used elevated temperature/vacuum pressure for emulsion solvent evaporation for the formation of inorganic oxide microparticles. The droplets shrink due to a difference between the vapor pressures inside and out. It in turn depends on the difference between the surface tension driven capillary pressure and the osmotic pressure mostly due to the dissolved salts according to the formula:

$$\Delta P = P_C - P_{Osm} = \frac{2\gamma}{r} - \left\{ \sum_i \rho_i(r) - \frac{kT[\kappa(r)]^3}{24\pi} \right\}$$

where $\rho_i$ is the number density of ionic species i and $\kappa$ is the Debye screening parameter. Both $\rho_i$ and $\kappa$ are known functions of the droplet radius. Setting $\Delta P=0$ gives an equation that allows an estimation of the minimal droplet radius that can be obtained for certain surface tension and concentration of ionic species. While there is some finite molecular solubility of dipolar water in an oil phase (which makes the evaporation process possible) it is highly unlikely that negatively charged DNA would be partitioned into the non-polar oil continuous phase.

Following ePCR and shrinking of the droplets to <1 μm in diameter, a droplet array will be created by depositing the droplets into ordered wells. Droplets may be captured in chambers having dimensions equal to the diameter of the encapsulated drops. One can use this method as a starting point for creating encapsulated droplet arrays to study selective wetting and DNA-substrate binding. However, this method may be limited by the number of droplets (about 8,000) that can be arrayed due to the large pressure drops that can be required to force large numbers of droplets through orifice restrictions in a linear microchannel.

One approach for forming high density arrays is to form patterned wells of photoresist epoxy on a glass substrate using interferometric photolithography. The pitch between wells can be 800 nm, which can allow for approximately 6 billion wells in a flowcell. Droplets used in traditional bead-based ePCR are large and automatically array under the force of gravity. However, our droplets after shrinkage can be less than a micron in diameter and, therefore, subject to Brownian forces. One approach for depositing the droplets could be to simply press a slide over the droplet system so that droplet deformation occurs, which would increase the surface extension energy by approximately: $E_s \approx \gamma \Delta A$, where $\Delta A$ is the increase in area created by sphere deformation. The excess extension energy may preferentially force the droplets into the wells to relax the applied stress and reduce the surface energy.

Another strategy is to place an electrode (e.g., indium tin oxide) below the surface of the array and contact a second electrode to the fluid to induce an electric field. The field can be supplied in such a way that it is much greater in the wells due to the well geometry, causing the droplets to preferentially move into the wells due to dielectrophoresis (FIG. 23). It has been shown previously that charged droplets in a non-polar dielectric oil phase can both electrophorese and can induce selective coalescence. Thus, the droplets may acquire a charge and move accordingly.

Once the droplets have been compartmentalized into the wells, wetting of the droplets on the streptavidin-functionalized glass surface can be induced via electric field application, serial dilution of the emulsifying surfactant, addition of an emulsion-breaking surfactant, or addition of alcohols. Once full wetting of the droplet on the streptavidin-coated glass is achieved, the amplified DNA can bind to the surface, and thus allow for sequencing using any polony sequencing tool proposed herein.

To achieve production rates on the order of $10^{10}$ monodisperse droplets in a reasonable time period, one may use an emulsification system capable of emulsifying large volumes. The microfluidic devices commonly used may not be sufficient (1000 droplets/sec) and, therefore, one may use emulsification technology membranes developed by Nanomi called MICROSIEVE membranes (http://www.nanomi.com/membrane-emulsification-technology.html). These membranes allow for the production of monodisperse microdroplets, scalable to any volume. This facilitates large-scale ePCR/Genomic sequencing by providing a platform to produce billions of droplet bioreactors in a reasonable amount of time, which is not currently possible with droplet based microfluidic systems.

The methods described herein can reduce the cost of sequencing the entire genome of an individual such as, for example, a human genome. Cost may be influenced by the total number of beads (or rolonies or emulsion array elements) being sequenced. This number is determined by the biochemistry cycle time. Current biochemistry runs about 70 minutes per cycle, and our best estimate of the biochemistry timing for the new proposed sequencing runs is 90 minutes.

Cost also may be influenced by the number of beads (or rolonies or emulsion array elements) per flowcell. Currently, one can image at a rate of approximately 28.5 frames per second or 35 msec exposure in continuous scanning mode. This means one can image 154,000 frames during the biochemistry cycle or 38,500 frames in four colors. When sequencing beads, one may be able to identify 45,000 beads in a single frame. Therefore, one may be able to sequence from $1.7\times10^9$ beads. It is realistic for 80% of the beads to provide clonal sequence following enrichment, resulting in $1.3\times10^9$ beads providing useful sequencing data. When sequencing rolonies or emulsion array elements, it may be possible to obtain a maximum of $6\times10^9$ features per flowcell. If 80% of these features will provide sequence, the result is that it may be possible to achieve $4.8\times10^9$ features providing useful sequence data.

Cost also may be influenced by read length. Using a fragment library, one can sequence paired ends of the fragment libraries (i.e., 72 bases). Using a mate pair library prepared using EcoP15I as the restriction enzyme, one can sequence 26 base mate pairs or 52 bases. Using a mate pair/fragment library sequenced using the QPePCR approach, one can sequence the paired ends of the mate paired approximately 100 bp fragments. From each fragment one can sequence 19+36 bases. Therefore, we expect to obtain 90 bases.

Dual Primer ePCR (DPePCR)

DPePCR enables paired-end sequencing of fragment libraries. To perform DPePCR, both forward and reverse primers are attached to 1 μm beads (FIG. 31B) that are included in a modified ePCR protocol. Additionally, since the amplicons are confined to the droplets, the amplification efficiency is increased by including free primers in the aqueous phase (FIG. 31C). After 120 PCR cycles, a single DNA fragment in an emulsion drop can be amplified effectively. After amplification, we have found the DNA to be highly stable in the double stranded state. Denaturing conditions will denature the DNA; however, since both strands are present on the bead, the double stranded state can immediately reform, which inhibits sequencing of the DNA. To overcome this issue, type IIs recognition enzyme sites (i.e. BceAI and AcuI) were placed at the ends of the amplicons being amplified immediately adjacent to the unknown sequence during library construction (FIG. 31A). The DPePCR product can then be digested with restriction enzymes (i.e. BceAI and AcuI), and capping adaptors are ligated to the free end of the dsDNA (FIG. 31D). This gives us the ability to sequence from both strands of the DPePCR using standard sequencing by ligation (SBL) (FIG. 31D).

The SBL sequencing strategy for DPePCR beads is similar to sequencing from standard ePCR beads (FIG. 31D). The difference is that since there are two paired-end fragments, both ends can be sequenced independently from both the 3'→5' and 5'→3' directions using four different anchor primers (FIG. 31D).

To validate the formation of strong double strand DPePCR product, the beads (following DPePCR) were treated with 0.1M NaOH without restriction enzyme digestion. After denaturing, a Cy5 labeled oligo (Cy5 labeled FDV2-PM—Example 4) was annealed to the bead-bound DNA fragment (Example 4). The results indicated that the Cy5 Oligo could not hybridize to the DPePCR product, which suggests the formation of double strand DPePCR product was in a "bridged" confirmation. Following restriction enzyme digestion, we were able to anneal the anchor primers (Example 4) and successfully sequence the DNA on the beads from both ends of the fragment.

Without wishing to be bound by any particular theory, it is believed that the DNA fragment on each bead arises from a single molecule in an emulsion and should therefore be clonal, which facilitates DPePCR. To validate the clonal amplification, we used DPePCR and SBL in the G.007 Polonator (Dover Instrument Corp., Westborough, Mass.) to sequence a *Streptococcus pyogenes* genome fragment library; when sequenced, the clonal amplified beads showed a single color during each SBL cycle (FIGS. 32A and 32B), which indicated the beads were clonal. Additionally, a random sampling of approximately $10^6$ reads were mapped to the *Streptococcus pyogenes* genome (GenBank Accession No. AE014074.1) to ensure we were sequencing paired ends. The reads were seven basepairs from the forward primer site, and 14 bp from the reverse priming site. To map to the *S. pyogenes* genome, the reverse priming site sequence was first mapped to both strands of the genome and then the complement of the forward priming site sequence was mapped to the strand on the genome where the reverse priming site sequence was found. Roughly, 25% of the reads mapped to the genome and the average separation between the paired ends in the genome was found to be approximately 100 bases (FIG. 32C), which is consistent with the size range that selected in the gel purification step of the library preparation (Example 4).

Additionally, as a final validation for the approach, we measured the library complexity. The complexity of the library is defined as the diversity of DNA molecules that are sequenced. For example, when a sequencing library is prepared and subjected to extensive amplification (PCR or Rolling Circle Amplification) the complexity is reduced. The fragment library was found to have high complexity, with >99% of the reads being unique, thus improving upon the traditional mate pair library production protocol.

In conclusion, we have presented an efficient dual primer emulsion PCR strategy for paired-end next generation sequencing, DPePCR. The DPePCR concept will be applicable to any next generation sequencing platform using emulsion PCR.

Re-Sequencing Genome Mapping Code

Mapping the sequenced tags back to the genome sequence comprises a major computational aspect of the whole genome re-sequencing process. Searching and aligning DNA sequences has received considerable attention; however, we now face an added challenge of mate paired short reads. The specific requirements of our re-sequencing efforts have been partially addressed and we will continue to improve our analysis code, as this capability is required since we continue to develop technologies with reads that are different from the other technologies.

Design.

The problem in this case requires the matching of short DNA sequence tags (current code handles 10-32 bases tags or 20-64 bases of sequence per bead) to a large mammalian sized genome (>$10^9$ bases). The basic algorithm consists of building a hash table from the parent sequence and searching for the tags in this hash table.

Hash Function.

We wrote a custom hashing function to convert the DNA sequence into an integer for optimal memory usage. Each nucleotide is represented by a two bit binary number: A=00, C=01, T=10, and G=11. For example, the sequence CATG is 01001011(base-2) or 75(base-10). The memory used by this hashing scheme is the absolute theoretical minimum required to store DNA sequence in memory. Based on this hashing scheme a 32-bit unsigned integer can be used to represent tags up to 16 bases in length. For the current application the query tag size is in the range 10-32 bases, so one (10-16 bp) or two (17-32 bp) 32-bit unsigned integers are used to represent each tag.

Creating Hash Table.

To create the hash table the parent genome sequence is scanned to find all tags of given size t. Each tag along with its location is stored as a [tag,locus] pair in an array. This [tag, locus] pair array constitutes the hash table and is generated in a single pass of the genome. The locus is stored as an 32-bit unsigned integer, therefore a total of 12 bytes are required for each [tag,locus] pair. Therefore for a genome sequence of size n the hash table requires 12(n−t) bytes.

Searching.

A Binary search algorithm is used to locate the query tag in the [tag,locus] hash table. The hash table is searched both with the original query tag and the reverse complement of the query tag. The sequence comparison is optimized and greatly accelerated by converting t sequences to integers, however the searching can still take a long time if a linear search is used because there are a large number of tags to search against a large sequence. Therefore, we sorted the array and performed a binary search which needs far fewer comparisons compared to a linear search (i.e., approximately $10^8$ comparisons worst case scenario vs or 27 or $\log_{2[}10^8]$ comparisons for 100 million tags).

Single Nucleotide Polymorphism (SNP) Detection.

To find SNPs, each nucleotide position in the query tag is substituted with all possible nucleotide bases to generate a new query tag. For example given a query tag of 18 bases, each base position can be substituted with 3 bases resulting in 54 new query tags. Since both forward and reverse complement is searched a total of 109 (54*2+1) searches are required to allow a single base mismatch in the query sequence. To reduce the computational demand we exploited the fact that each query is comprised of two mate paired tags. Since the mismatch substitutions are done only on one tag at any time, first the non-substituted query tag is searched and only when a match is found are the substitutions on the other tags carried out (approximately 10× performance improvement).

Additional Code Optimizations.

Aside from the hash table and searching algorithms that we developed, additional code optimizations have been implemented resulting in significant speed and memory enhancements. First, separate sub-routines for small and large tags were used. This allows using a single 32-bit unsigned integer to store small tags (1-16 bases) while using two 32-bit unsigned integers for long tags (17-32 bases). This results in a 33% lesser memory usage for small tags. Second, Standard Template Library (STL) functions in C++ are used for common tasks such as sorting etc. STL implementations are highly optimized and out perform almost all third party libraries and hand coding. Third, lookup tables and binary operations were used in frequently called sub-routines. For example, in calculating the hash value for each base, multiple if-else statements can be replaced by single array lookup statement. Fourth, since all low level computing is in binary, combining several arithmetic operations into a single binary operation results in far fewer CPU cycles being used. We implemented a binary operation to calculated the complementary DNA sequence. Fifth, several compiler level optimizations were enabled, namely: sse3, which uses the latest sse3 instructions set to generate code optimized for Dual-Core Intel Processors; inlining, which removes function call overhead by inlining functions; and loop unrolling, which replaces loop operations with vectorized operations. Sixth, parallelization—the code has been parallelized using the OpenMP command directives. OpenMP parallelization allows multiple simultaneous threads (Multithreading) to execute. Due to the iterative nature of tag searching problem, parallelization provides near theoretical level performance gains. For example, tag searching is almost four times faster when running on a four processor machine as opposed to a single processor machine with similar hardware. Also, the software has been compile on both Windows and Linux and runs in 64-bit mode in order to load the entire human genome into the hash table and perform SNP finding on the human genome.

Combination Sequencing Methods

In another aspect, the invention relates to sequencing a complex mixture of nucleotide fragments (e.g., genome fragments), by a two-step combination sequencing protocol. First, at least five bases of the end of a fragment are sequenced, thereby identifying the fragment as one of a limited number of possible fragments. Second, at least a apportion of the remainder of the fragment is sequenced using Sequencing By Hybridization. Generally, the method involves fragmenting a large, complex nucleic acid molecule into a plurality of fragments approximately 300 to approximately 500 bases in length. At least one end of each fragment is at least partially sequenced, allowing one to uniquely—or nearly uniquely—identify each fragment as part of a known sequence. Then, Sequencing-by-Hybridization of at least a portion of the remainder of the fragment can uniquely identify the fragment and/or identify differences in the sequence compared to a known reference sequence.

One or both ends of the fragment maybe sequenced. Moreover, sequencing a greater length of one or more ends can provide additional sequence information to improve the identification of the fragment against a known reference sequence. In practice, however, sequencing at least five to at least ten bases of one end of the fragment can limit the possible fragment matches against a known reference sequence and, indeed, may be sufficient to uniquely identify the fragment against the known reference sequence. Sequencing beyond, for example, 20 bases is possible, but the additional fragment identification information generated may not by useful enough to offset the efficiency of the overall combination sequencing method.

The sequencing of at least one end of the fragment and Sequencing-by-Hybridization can be performed on more than one fragment. Thus, the method may be used to, for example, rapidly sequence a large, complex nucleic acid sequence such as, for example, an entire genome.

For brevity, the description that follows describes a combination sequencing protocol that involves using Sequencing-by-Ligation for determining the sequence of the end of each fragment. However, other sequencing methods may be used to sequence one or both ends of the fragment. Suitable alternative methods for sequencing one or both ends of the fragment include for example, Sanger sequencing. Therefore, while the description specifies sequencing one or both ends of a fragment using Sequencing-by-Ligation, the combination sequencing method includes sequencing one or both ends of a fragment by any suitable method.

In another aspect, the invention includes an ultra-high throughput method that combines Sequencing-by-Ligation (SBL, described above) and Sequencing-by-Hybridization (SBH). Current polony sequencing technology is well-advanced; the SBL approach described above can generate approximately 26-30 bases from approximately 1.6 billion 1 micron beads simultaneously, and a single sequencing run takes approximately four days to complete. Therefore, one has the potential to generate 48 billion bases of sequence in approximately four days. Typically, however, one can generate about 6 billion bases of mappable sequence in four days. With the combined sequencing strategy, one can increase throughput by approximately 10-fold, perhaps further.

One way to further improve the throughput of polony sequencing and other next-generation sequencing technologies is to increase the number of elements that are sequenced or increase the density of the beads. However, since the beads are a fixed size (1 μm in diameter), the ability to increase density is limited. Therefore, to increase the density beyond the limits imposed by bead diameter, one can use an alternative to beads. One can modify a RCA colony or "Rolony" approach by binding the rolonies to a patterned array to maximize the density as described above and illustrated in FIG. 20. The combination DNA sequencing technology has the potential to significantly impact health care, both directly by providing diagnostic and prognostic markers for the clinical setting, and indirectly by accelerating the pace of basic and clinical biomedical research.

Requirements of an ultra-high-throughput sequencing technology include: (a) cost per raw base, (b) throughput per instrument, (c) accuracy per raw base, and (d) read-length per independent read. The combination sequencing approach can provide a low cost, robust, human genome sequencing method. The remaining sequencing requirements are highly interdependent. For example, the error rate of an ultra-high-throughput sequencing method must be considerably lower than the level of variation that one is trying to detect. Since there is approximately 1 base difference in every 1,000 bases, an exemplary acceptable error rate can be, for example, 1 error per 10,000 bp. The combination sequencing method can generate raw sequence with an error rate of better than 99.0% accuracy. Thus, 3× coverage of each base can yield an error rate of approximately 1/10,000 bp, which meets the exemplary acceptable error rate. In order to ensure a minimum 3× coverage of >95% of the human genome, one must sequence the human genome to a minimum of approximately 6.5× coverage, or approximately 40 billion raw bases of sequence.

The combination sequencing method is novel and innovative. Sequencing by hybridization (SBH) was originally developed to sequence a single DNA fragment by hybridizing the DNA fragment to an array containing nucleotide probes corresponding to all possible sequences of a given length. However, successful implementation of the concept employed in combination sequencing method described herein, which reverses the fragment and the probes in order to sequence unknown DNA sequences, is novel. In other words, the genome fragments are placed on an array or surface, and all possible combinations of an oligonucleotide (e.g., a 5-mer, 6-mer, 7-mer, etc.) are sequentially hybridized to the immobilized fragments. Prior to the description herein, SBH has been inadequate to successfully and accurately identify new SNPs and genetic variants because the SBH strategy was not robust for sequencing an entire bacterial genome. The combination sequencing approach can identify all of the genomic DNA fragments in the array prior to SBH using the SBL data. Therefore, complex genomes can be sequenced by SBH because the SBH will be used to only re-sequence many (billions) of known 300-mers. The combination sequencing approach can allow for nearly a 1 Terabase per sequencing run, especially when combined with a method for increasing feature density.

One embodiment of the combination sequencing strategy for sequencing the entire approximately 300 base genomic DNA fragment is shown in FIG. 30. This embodiment employs a combination of Sequencing-by-Ligation (SBL) and Sequencing-by-Hybridization (SBH). The SBH portion of the strategy is based on hybridization of 5-mers to the immobilized DNA. However, all potential 5-mers have significantly different Tm values. Therefore, random bases are added to the ends to raise the Tm values to make the hybridizations possible. Additionally, buffer conditions are optimized for normalization of the Tm values. Finally, conditions are optimized to promote correct hybridization but eliminate non-specific interactions.

We have performed simulations on Chromosome 1 to determine how uniquely the potential genome fragments would map back to the genome. The results in FIG. 27 show that to uniquely map >90% of the fragments to the genome we need to obtain reads of 10 bases in the direction and 16 bases in the direction (i.e., 26 total bases). Note, this figure is only for a single chromosome, based on additional simulations, we know that we need to increase the 3'→5' read length to at least 16 bases to uniquely map >90% of the fragments to the genome.

The SBH approach is then used to sequence the entire length of the genome fragments. The SBH technique will use SBL paired-end reads to facilitate the SBH (FIG. 30). The SBH technique is illustrated in FIG. 28. Hybridization of all possible oligonucleotides of a given length to an unknown strand can be used to decipher the sequence. The advantage of our approach is that we will be resequencing the known fragments that are first identified by SBL. Therefore, we will be able to sequence the entire human genome using only 5-mer probes, since we will essentially only be resequencing 300-mer fragments.

Data in FIG. 29 shows that correct 5-mers will hybridize while even a single mismatch will destabilize the hybridization.

We will hybridize all possible oligonucleotides of the given probe length (total number=$4^N$). We intend to utilize 5-mers with 1-2 random bases added to the ends, depending on Tm of the 5-mer probe region. Thus, the actual length of the probes is between seven and nine bases. We nevertheless refer to the probes as 5-mers because only five bases are used in the sequencing; the extra degenerate bases are to raise the Tm.

Typically in SBH techniques, the probes can include LNA bases to increase the Tm. We have used locked nucleic acid (LNA) for all five of the hybridization bases in the probes. The terminal random bases may be LNA or DNA bases. In some cases, the probes can include a combination of LNA bases and DNA bases to achieve a desired Tm value such as, for example, a Tm of at least 8° C. In other cases, if needed, one can increase the length of the random regions.

In some embodiments, the number of random bases in the probes may vary. For example, a high GC probe may include 1 or 2 degenerate bases, but high AT probes may include an additional degenerate base. However, based on the results shown in FIG. 29, buffer conditions can be modified to allow all probes to hybridize efficiently. For example, TMAC (tetramethylammonium chloride) buffer to normalize the Tm contribution of A/T and G/C base pairs. Other salt buffers such as, for example, those containing $Mg^{++}$ ions also may be suitable. In some embodiments, different buffers may be used for different probes.

SBH can be performed at any suitable temperature. In some embodiments, the temperature of the flowcell can be from about 10° C. to about 60° C., although the SBH technique may be performed under appropriate conditions at temperatures outside of this range. The temperature for each 5-mer can be tuned independently. Hybridizations may be performed in pools of four probes, which can be temperature matched for their hybridization characteristics.

Generally, the buffer, temperature, probe nucleotides (LNA vs. DNA), number of random nucleotides, temperature can be selected to establish a desired Tm value such as, for example, a Tm value of at least 8° C. while limiting the frequency of false positives.

SBH sequences may be read by comparing SBH sequence variants to a reference sequence. For each bead and/or rolony, one can determine a hybridization spectrum, which is a vector of normalized hybridization intensity across the complete set of probes. Since the SBL reads from each end of each fragment is known; one can calculate the "ideal" hybridization spectrum by mapping the SBL reads to the genome (using our code or other mapping packages, such as Bowtie). When multiple potential fragments are identified by SBL read mapping, one can use the hybridization spectrum to identify the correct fragment as described in more detail below. The identification of the correct fragment can be made by identifying the maximal dot product between the hybridization spectrum and the "ideal" hybridization spectrum. To identify SNPs, one can search for the most likely set of genetic variants relative to the reference given the experimentally determined hybridization spectrum.

Basecalling can be performed by examining each base in the genome individually and determining if any base substitution will provide an increase in the match between all overlapping reads (accounting for heterozygous calls). The approach works well because for each base substitution, there will be five probes that were originally absent that are now present, and five probes that were originally present that will now be absent, so up to 10 elements of the hybridization spectrum could be changed. From the SBH data, one can calculate the average intensity of all probes from the aligned reads that contain the base, and calculate an average intensity which will allow us to calculate a posterior log-odds of a substitution for each probe that would be inserted into the hybridization spectrum if the substitution were accurate and subtract the log-odds for the probes that would be eliminated from the hybridization spectrum if the substitution were there. Then, the cumulative log odds for each probe is summed to give a log-odds for a substitution. SBL+SBH can allow one to identify unknown SNPs more easily and more accurately than prior methods that include an a priori P term in the analysis based on known SNP frequencies in the population. Finally, one can define a quality score to provide a mapping to Phred scores. The quality can be defined as the difference between the most likely base and the second most likely base and the conversion to Phred score can be performed as previously described.

The minimum SBL read length to reach a minimum of 95% coverage of the human genome can be determined as follows. One can generate a complete data set with at least 28 total bases, then repeat the analysis using successively shorter reads to generate a plot that shows the coverage versus SBL read length. In some embodiments, it may be preferred to use the shortest SBL read length required to generate at least 95% coverage of the genome—i.e., 99.99% accurate calls for 95% of the genome.

In some embodiments, the probe region can include four bases, thereby decreasing the time necessary for the run because it would reduce the number of hybridizations. In order to obtain meaningful hybridization spectra for 4-mer probes, the genome fragment length may be decreased. For example, a 4-mer probe set may work for fragments of, for example, from about 150 bases to about 200 bases in length, based on the observation that the hybridization spectrum will change for most randomly chosen 150-200 base fragments from the genome if a SNP is present. If one reduces the fragment length by 30%-50%, one can decrease the sequence generated per run. However, the resulting increase in sequencing rate and/or decrease the cost of SBH probes may more than offset the decreased sequence generated per run.

Matching the time needed for the sequencing biochemistry and for imaging can increase the efficiency of data acquisition. Biochemistry times can be matched to the imaging time using SBH biochemistry because the majority of the cycles will be SBH. Exemplary SBH biochemistry typically consists of one strip and hybridization. Exemplary current strip and hybridization times are about 40 minutes per cycle. Imaging time can be influenced by the size of the flowcell and, therefore, the number of beads or rolonies per flowcell. An exemplary image rate can be, for example, approximately 28.5 frames per second or 35 msec exposure in continuous scanning mode. At such an exemplary imaging rate, one can image 154,000 frames during the biochemistry cycle or 38,500 frames in four colors. When sequencing beads, one can identify 45,000 beads in a single frame. Thus, one can sequence from $0.6\times10^9$ beads/flowcell (80% of the max) or $1.2\times10^9$ beads per dual flowcell. When sequencing rolonies, one can obtain a maximum of $2.8\times10^9$ features per flowcell. Thus, at 80% of max, one can sequence approximately $4.4\times10^9$ rolonies per dual flowcell.

The present invention is illustrated by the following examples. It is to be understood that the particular examples, materials, amounts, and procedures are to be interpreted broadly in accordance with the scope and spirit of the invention as set forth herein.

EXAMPLES

Example 1

We can currently sequence 26 to 30 total bases per bead in a polony sequencing run (only up to 8 continuous bases). Increasing the read length has proven difficult. We have been able to extend our reads in proof-of-concept experiments and we are now implementing these in the Polonator G.007 flow cell (Dover Systems, Salem, N.H.). Our goal in this Aim is to extend the reads to obtain 36 bases of continuous sequence. This will allow us to sequence 72 bases per bead from a fragment library (described in Example 2).

Increasing the Read Length Using Cyclic Ligations

The Endonuclease V cleavage of deoxyinosine in the nonamer is now working very well and we have sequenced 18 continuous bases on beads in suspension. We anticipate being able to extend the reads to 36 continuous bases or more.

Optimizing Ligation Efficiency

The Endo V cleavage is extremely efficient, we can no longer detect signal from beads that were previously saturated after 10 minutes digestion with a very dilute enzyme mix. However, the ligation efficiency is not as high. In solution, we have been able to perform ligations with approximately 95% efficiency (measured by the out of phase signal that is obtained on the second extended ligation. However, in a flowcell the efficiency drops to about 80%. This does not cause a phasing problem, because we are able to eliminate out-of-phase signal by phosphatase treating and removing the 5' phosphates from the unextended primers.

To increase the efficiency of the ligation, we have taken the following approaches. We have used fluorescent nonamer ligation. Fluorescent nonamer ligation efficiency is sufficient for signal on 1 cycle (up to 8 bases), but we could improve this to increase signal on the second round of ligation. In solution we found that the following increased efficiency (a) increased time up to 1 hr, (b) increase ligase concentration, (c) repeated ligations, and (d) inclusion of PEG in the ligase buffer. We have also tried following the initial ligation with a saturation oligo that does not contain a fluor, but has a deoxyinosine at the $7^{th}$ base. We have found that the ligation efficiency of the saturation oligo is increased if we use an 8-mer (not a 9-mer) and Endo V is able to cut correctly with only a single base 5' to the deoxyinosine.

Alternatively, one can mix the ligation reaction in a flowcell using, for example, a syringe pump. On beads in solution, one can mix the reaction every few minutes by vortexing. However, one is unable to vortex the reaction in a flowcell. One can, however, achieve mixing the reaction in the flowcell using a syringe pump.

Optimizing Digestion Efficiency

We have optimized the digestion efficiency in solution. We determine the minimal digestion to cut the deoxyinosine and not non-specifically digest the DNA on the beads. We have performed over 20 cycles of Endo V digestion on beads in solution without significant degradation of signal. We have also digested the beads overnight in an Endo V digestion with significantly less, if any, DNA damage. We: (1) determine minimal time required to digest, (2) use 3M guanidine in the wash buffer, which is sufficient to inactivate Endo V and not damage our DNA or denature the DNA on our beads, (3) use SDS in the wash buffer, which is also capable of inactivating Endo V, and/or (4) include short random DNA, which protects the DNA from non-specific degradation and does not impair specific digestion of the deoxyinosine.

Optimizing Phosphatase Reaction

We have also already optimized the efficiency of this reaction in solution and it appears to work in the flowcell. We reduce to the extent possible—in some cases to the extent of eliminating—phosphatase activity so that phosphates are not removed, for example, following Endo V digestion. Each of the 3M guanidine and SDS in the wash buffer is capable of inactivating any residual phosphatase.

Validation

One can validate the sequencing approach by two methods. First, one can sequence known templates directly loaded on the beads. This can provide a good approach for optimizing the sequencing, but it may not be sufficient to truly validate the approach. Therefore, one can sequence paired ends from a fragment library from Group A *Streptococcus* (GAS) genome, prepared using the Dual Primer ePCR (described in Example 2). Extensive polony sequencing data on GAS is available for comparison. One can measure the coverage of the genome and the accuracy of the approach to ensure that there is not significant bias or errors present when sequencing using this approach. One can also look at the error rate as a function of position in the read (FIG. 8) to ensure the data quality is maintained during each cycle.

Example 2

The first step in preparing a library is typically size selection, and this could ultimately be performed by HPLC, or even eliminated by starting with a more uniformly sheared DNA sample. A single gel could be run to verify the size for data analysis at the end. One can uniformly shear DNA with a nebulizer generating a narrow size range of approximately 700-1300 bp.

We have developed a bead based strategy for purifying the restriction digestion product fragment that eliminates the need for PAGE purification, illustrated in FIG. 13.

Following the bead-based purification, the fragments are affixed toe the beads and available for ligation of end adaptors. Having the fragment on beads simplifies all following steps since the beads can be moved from step to step by thoroughly washing the beads.

The final library is obtained and bead bound. At this point the library has undergone zero amplification. One can amplify the library directly off the beads using PCR to generate the final library. The resulting PCR products can be very clean and a final PAGE purification can be unnecessary. A diagnostic PAGE gel may be run at this stage to confirm correct library size and/or confirm that no other fragments are amplified.

One can generate a library in two days using the protocol described in FIG. 13.

Dual Primer ePCR

Dual Primer ePCR or DPePCR is an effective way to perform paired end sequencing of a fragment library. The DPePCR approach is described in FIG. 16, and the paired end sequencing strategy for a fragment library is shown in FIG. 26. The restriction enzyme MmeI is effective on the DPePCR primers and allows sequencing out to 19 bases from each end of the library molecule. MmeI Type IIS restriction enzyme (e.g. Fold) cleave DNA at a defined distance from their non-palindromic asymmetric recognition sites.

Use of the restriction enzyme EcoP15I for the digestion can allow for 26 bases reads. EcoP15I is, however, a different class of enzyme (type III) and it requires two recognition sequences on the continuous DNA strand to cut. Also, ideally, the sites are oriented inversely (head-to-head). One or more of the following adjustments may be performed when using EcoP15I as the restriction enzyme. The sites may be inversely oriented such that the cut site for one would be beyond the 5' end bound to the beads. This may interfere with the cutting, so one may further include free DNA with the EcoP15I recognition sequence. The free DNA can allow for cutting, but likely with reduced efficiency. Second, one can incorporate the MmeI site on one of the primers and, therefore, one side will have 19 bases for sequencing, but the other strand will contain the rest, allowing us to sequence as far as possible. For example, if we obtain 36 base continuous reads, we will be able to sequence a fragment library with paired end reads of 19 and 36 bases (55 total bases).

Quad Primer ePCR (QPePCR)

Quad Primer ePCR (QPePCR) advances the technology so one may sequence essentially sequence mate paired fragment libraries (FIGS. 16 and 26). One would typically utilize the library prep protocol for preparing approximately 100 base paired libraries. One can perform QPePCR to generate beads that contain fragment libraries as described above. We plan to then paired end sequence both of these fragments as described above, with the added benefit that the fragments are mate paired.

QPePCR can essentially quadruple sequencing capacity. For example, 18 continuous bases may be sequenced with the dI approach described in Example 1. Using QPePCR, we could sequence 4×18 bases/bead or 72 bases. This significantly advances polony sequencing technology and reduces the cost associated with sequencing an entire genome.

Example 3

Bead Enrichment

Bead enrichment may be accomplished by modifying standard methods as follows. The beads can be treated with exonuclease I after ePCR and before enrichment. The exonuclease I treatment can eliminate unextended primers and, therefore, can reduce non-specific interactions that can interfere with the enrichment. Also, TE buffer with 0.1% triton-X and 50 mM NaCl can provide for more stringent hybridization between beads with DNA and enrichment beads. For the DPePCR and QPePCR we will follow a different enrichment strategy that we anticipate will effectively enrich for DNA coated beads. The approach is illustrated in FIG. 19.

Example 4

A DPePCR library was prepared by fragmenting the *S. pyogenes* genomic DNA by Fragmentase (New England Biolabs, Inc., Ipswich, Mass.) and PAGE purifying ~100 base pair genome fragments. The DNA was blunt ended (End-Repair Mix, Enzymatics, Inc., Beverly, Mass.) and A-tailed (Taq Polymerase, New England Biolabs, Inc., Ipswich, Mass.). Then FDV2-BceAI-Primer-F/R and RDV2-AcuI-Primer-F/R (preparation of which are described below) were ligated to the DNA fragments, heated to 94° C. for two minutes, and PCR amplified for 13 cycles as follows: 94° C. for 30 seconds, 58.8° C. for 30 seconds, 72° C. for 90 seconds, repeating the 94° C.-58.8° C.-72° C. cycles 13 times, 72° C. for five minutes, then held at 4° C. The PCR products were then PAGE purified to isolate the DPePCR library.

To amplify the library by DPePCR for sequencing, 2 μL of the fragment library, prepared at an appropriate concentration to allow single molecule per drop, was mixed with 265 μL DPePCR master mix (preparation of which are described below), 13 μL of JumpStar Taq (20,000 U/mL), 0.1 μM FDV2-Short-Unmodified-Primer and 0.1 μM RDV2-Short-Unmodified-Primer and 20 μl, Dual Primer beads (preparation of which are described below). The mixture was added to 400 μl, Silicone Oil Phase in a 2 mL tube and put on a TissueLyser II (Qiagen Inc., Valencia, Calif.) to emulsify (19 Hz for 90 seconds). The DPePCR emulsion mixture was aliquoted to three 650 μL tubes and thermocycled as follows: 94° C. for two minutes, 90° C. for 15 seconds, 56° C. for two minutes, 72° C. for 45 seconds, 99 repeats of the 90° C.-56° C.-72° C. cycle, 90° C. for 15 seconds, 61° C. for five minutes, 19 repeats of the 90° C.-61° C. cycle, 72° C. for five minutes, then held at 4° C.

The emulsion beads were broken and cleaned by adding 400 μL silicon oil to original PCR tubes, vortexing, and pooling into 1.5 mL tubes. The tubes were spun one minute at top speed to remove aqueous wash two more times with 500 μL silicon oil. The beads wee washed three times as follows:

1) 300 μL 100% isopropanol, with tubes placed on MPC to allow the beads to collect, 2) 300 μL 80% EtOH/annealing buffer, 3) 300 μL 1×NXS, then 4) 300 μL 1×TE/0.01% Triton. Finally, the beads were suspended in 100 μL TE with 0.01% Triton.

The DPePCR beads were digested with 5 μL AcuI (5000 U/mL) (New England Biolabs, Inc., Ipswich, Mass.), 0.8 μL S-adenosylmethionine (SAM) (32 mM) and 394.5 μL 1× NEBuffer 4 by incubating at 37° C. for 60 min. After AcuI digestion, the beads were washed 3× with NXS buffer (10 mM Tris.Cl, pH 7.5; 1 mM EDTA, pH 8.0; 100 mM NaCl; 1% Triton X-100) and TE with 0.01% Triton, and digested with 4 μL BceAI (1000 U/mL) (New England Biolabs, Inc., Ipswich, Mass.), in 392 μL 1× NEBuffer 3 plus 4 μL Bovine Serum Albumin (10 mg/mL, New England Biolabs, Inc., Ipswich, Mass.) at 37° C. for 60 minutes. After BceAI digestion, the beads were washed three times with NXS and TE with 0.01% Triton. Before ligating capping adaptors, the beads were treated with 2 μl, Antarctic Phosphatase (5000 U/mL) (New England Biolabs, Inc., Ipswich, Mass.) in 198 μL 1× Antarctic Phosphatase Reaction Buffer at 37° C. for 60 minutes to remove 5' phosphoryl groups from nucleic acids. After dephosphorylation, the beads were washed three times with NXS and TE with 0.01% Triton. For capping adaptors ligation, the beads were incubated with 2.5 μL AcuI-PlusPrimer-3' over-FIR (50 μM), 2.5 μL BceAI-PlusPrimer-3' over-F/R (50 μM), 2 μL T4 DNA ligase (600,000 U/mL) (Enzymatics, Inc., Beverly, Mass.) and 193 μL, 1× quick ligation buffer (Enzymatics, Inc., Beverly, Mass.) at room temperature for 60 minutes. The beads were treated with 0.1M NaOH and washed three times with 1×SSPE (Fisher Scientific, Pittsburgh, Pa.).

The DPePCR beads were sequenced from the FDV2 and RDV2 strand respectively using the same strategy from both the 3'→5' and 5'→3' directions. For test sequencing of the FDV2 strand in 3'→5' direction, the beads were resuspended in 135 μL 1×SSPE with 15 μL anchor primer FDV2-PM (100 μM), incubated at 70° C. for 5 minutes, 50° C. for 5 minutes and 25° C. for 5 minutes, and washed three times with 1E buffer (10 mM Tris.Cl, pH 7.5; 50 mM KCl; 2 mM EDTA, pH 8.0; 0.01% (v/v) Triton X-100). Then, 1 μL T3 DNA ligase (Enzymatics, Inc., Beverly, Mass.) and 200 μL ligation buffer (2 μL of each nonamer (300 μM) (Integrated DNA Technologies, Inc., Coralville, Iowa) and 200 μL 1×DNA quick ligase buffer (Enzymatics, Inc., Beverly, Mass.)) were added to the beads and incubated at room temperature for 30 minutes. The beads were then washed with 1E buffer and resuspended in 50 μL 1E for observation on fluorescent microscope. For test sequencing of the RDV2 strand in direction, the beads were treated with 0.1M NaOH and then hybridized anchor primer RDV2-PM and ligated nanomers using the same protocol as FDV2 strand. For 5'→3' direction sequencing, the beads need to be capped with dideoxynucleotide before hybridization and ligation. The capping reaction is performed by mixing the beads with 15 μl $CoCl_2$ (2.5 mM), 114 μL dd$H_2O$, 15 μL 10× Tailing buffer, 4 μL dideoxynucleotide mix (1.25 mM each dideoxynucleotide), 2 μL terminal transferase (20000 U/mL) (New England Biolabs, Inc., Ipswich, Mass.) and incubating at 37° C. for 60 minutes. The beads are then washed three times with NXS, 1×TE with 0.01% Triton, and PBS.

Bind Forward and Reverse PCR Primers to Microbeads Prior to DPePCR

PCR primers were bound to microbeads in a 1.5 mL tube. 240 μL B&W buffer (5 mM Tris.Cl, pH 7.5; 0.5 mM EDTA, pH 8.0; 1.0 M NaCl) was added to 240 μL MyOne streptavidin beads (Invitrogen Corp., Carlsbad, Calif.) and mixed by inversion. Place on magnetic particle collector to remove liquid by pipetting. Beads were washed two times with 480 μL of B&W buffer, then resuspended in 480 μL of B&W.

4.8 μL of 1 mM FDV2-dual biotin and RDV2-dual biotin primers were mixed, then added to the beads, vortexed, and incubated at room temperature for 20 minutes with mixing. The beads were washed three times with 600 μL of B&W buffer, then resuspended in 640 μl, of Tris-EDTA buffer.

Silicone Oil Phase

The silicone oil phase was prepared by mixing 10 g silicone oil AR20 (Sigma-Aldrich, St. Louis, Mo.), 7.5 g DOW CORNING 749 FLUID (Dow Corning Corp, Midland, Mich.) and 7.5 g DOW CORNING 5225 FORMULATION AID (Dow Corning Corp, Midland, Mich.). The oil phase was vortexed and immediately aliquoted into single use tubes.

Preparation FDV2-BceAI-Primer-F/R (50 μM), RDV2-AcuI-Primer-F/R (50 μM), AcuI-PlusPrimer-3' over-F/R (50 μM), BceAI-PlusPrimer-3' over-F/R (50 μM)

Anneal Primers:

Primer mixtures of 20 μl, FDV2-BceAI-Primer-F (100 μM) and 20 μL FDV2-BceAI-Primer-R (100 μM); 20 μL RDV2-AcuI-Primer-F (100 μM) and 20 μL RDV2-AcuI-Primer-R (100 μM); 20 μL BceAI-PlusPrimer-3' over-F (100 μM) and 20 μL BceAI-PlusPrimer-3' over-R (100 μM); and 20 μL AcuI-PlusPrimer-3' over-F (100 μM) and 20 μL AcuI-PlusPrimer-3' over-R (100 μM), respectively, were mixed, heated to 80° C. for two minutes, and then annealed by cooling. The cooling was performed by gradually decreasing the temperature as follows: 70° C. for two minutes, 60° C. for five minutes, 50° C. for five minutes, 40° C. for five minutes, 30° C. for five minutes, 20° C. for five minutes, then held at 4° C.

Library PCR Master Mix

| Reagent | Final Concentration |
|---|---|
| 10x Jumpstart Buffer | 1x |
| dNTPs | 0.2 mM |
| FDV2-BceAI-PCR | 0.5 μM |
| RDV2-AcuI-PCR | 0.5 μM |
| Jumpstart Taq | 0.01 U/μl |
| M B Water | — |

Dual Primer ePCR Master Mix

| Reagent | Final Concentration |
|---|---|
| 10x EXT | 1.2X |
| MgCl2 (50 mM) | 7.0 mM |
| dNTPs (10 mM) | 1.0 mM |
| Triton (10%) | 0.1% |
| BSA (10 mg/ml) | 1 mg/ml |
| FDV2 short unmodified primer | 0.1 μM |
| RDV2 short unmodified primer | 0.1 μM |
| Glycerol (50%) | 5% |
| JumpStart Taq | 0.1 U/μl |
| M B Water | — |

| Oligos | |
|---|---|
| Primers | Sequence |
| **Library Preparation Primers** | |
| FDV2-BceAI-Primer-F | 5'AACCACTACGCCTCCGCTTTCCTCTCTATGTCTACTAGTCAACGGCT-3' (SEQ ID NO: 1) |
| FDV2-BceAI-Primer-R | 5'-/5Phos/GCCGTTGACTAGTAGACATAGAGAGGAAAGCGGAGGCGTAGTGGTT/3AmMO/-3' (SEQ ID NO: 2) |
| RDV2-AcuI-Primer-F | 5'-ATATGTCAACTGCCCCGGGTTCCTCATTCACTCATGACTACTGAAGT-3' (SEQ ID NO: 3) |
| RDV2-AcuI-Primer-R | 5'-/5Phos/CTTCAGTAGTCATGAGTGAATGAGGAACCCGGGGCAGTTGACATAT/3AmMO/-3' (SEQ ID NO: 4) |
| FDV2-BceAI-PCR | 5'-AACCACTACGCCTCCGCTTTC-3' (SEQ ID NO: 5) |
| RDV2-AcuI-PCR | 5'-CTGCCCCGGGTTCCTCA-3' (SEQ ID NO: 6) |
| **Emulsion Primers** | |
| FDV2-dualbiotin | 5'-/52bio/TTTTTTTTTTTTTTTTTTTTTTTTTTTTTTTTTTTTTTTAACCACTACGCCTCCGCTTTCCTCTCTATG-3' (SEQ ID NO: 7) |
| RDV2-dualbiotin | 5'-/52bio/TTTTTTTTTTTTTTTTTTTTTTTTTTTTTTTTTTTTTTTTTTTTTTTTTTTTTTTTTTTTTTTTTTTTTTTTTTTTTTTTTTTTATATGTCAACTGCCCCGGGTTCCTCATTC-3' (SEQ ID NO: 8) |
| FDV2-short-unmodified-primer | 5'-AACCACTACGCCTCCGCTTTCCTC-3' (SEQ ID NO: 9) |
| RDV2-short-unmodified-primer | 5'-ATATGTCAACTGCCCCGGGTTCCT-3' (SEQ ID NO: 10) |
| **Capping Oligos** | |
| BceAI-PlusPrimer-3'over-F | 5'-/5Phos/NNTATCACTCAGACTATACTCTAAACCA-3' (SEQ ID NO: 11) |
| BceAI-PlusPrimer-3'over-R | 5'-TAGAGTATAGTCTGAGTGATA/3AmMO/-3' (SEQ ID NO: 12) |
| AcuI-PlusPrimer-3'over-F | 5'-/5Phos/TCTACATATTCTACCATCTACTTATCACACA-3' (SEQ ID NO: 13) |
| AcuI-PlusPrimer-3'over-R | 5'-GATAAGTAGATGGTAGAATATGTAGANN/3Phos/-3' (SEQ ID NO: 14) |
| **Anchor Primers** | |
| FDV2-PM | 5'-/5Phos/AGCCGTTGACTAGTAGAC-3' (SEQ ID NO: 15) |
| RDV2-PM | 5'-/5Phos/ACTTCAGTAGTCATGAGT-3' (SEQ ID NO: 16) |
| BceAI-Plus-Anchor Primer | 5'-TAGAGTATAGTCTGAGTGATA-3' (SEQ ID NO: 17) |
| AcuI-Plus-Anchor Primer | 5'-GATAAGTAGATGGTAGAATATGTAGA-3' (SEQ ID NO: 18) |

-continued

| Sequencing nonamers |
|---|
| -1 sequencing nonamers |
| 5'-Cy5-NNNNNNNNT (SEQ ID NO: 19) |
| 5'-Cy3-NNNNNNNNA (SEQ ID NO: 20) |
| 5'-TexasRed-NNNNNNNNC (SEQ ID NO: 21) |
| 5'-FAM-NNNNNNNNG (SEQ ID NO: 22) |
| +1 sequencing nonamers |
| 5'-/5Phos/TNN NNN NNN/3Cy5/-3' (SEQ ID NO: 23) |
| 5'-/5Phos/ANN NNN NNN/3Cy3/-3' (SEQ ID NO: 24) |
| 5'-/5Phos/CNN NNN NNN/3TxRed/-3' (SEQ ID NO: 25) |
| 5'-/5Phos/GNN NNN NNN/3FAM/-3' (SEQ ID NO: 26) |

All other nonamers (−2, −3, −4, −5, −6, −7, +1, +2, +3, +4, +5, +6) are generated by moving the fixed base. All nonamers were HPLC purified and degenerated bases were hand mixed to the 25:25:25:25 ratio.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for obtaining the sequence of a polynucleotide, the method comprising:

providing a polynucleotide library comprising a plurality of polynucleotide fragments immobilized to a substrate, wherein providing the polynucleotide library comprises:

fragmenting a nucleic acid molecule, thereby producing a plurality of nucleic acid fragments;

ligating a first end PCR primer to a first end of at least one fragment, and a second end PCR primer to a second end of the at least one fragment; and sequencing the ends of the at least one fragment, thereby identifying each of the at least one fragment as part of a known sequence;

hybridizing a first probe having known nucleic acid sequences to at least a portion of the immobilized polynucleotide library fragments;

identifying at least a portion of the first probe hybridized to the immobilized polynucleotide library fragments;

assigning to each hybridized fragment a nucleic acid sequence that is the complement of a plurality of nucleotides of the nucleic acid sequence of the first probe hybridized to the immobilized polynucleotide library fragment, wherein the assigning does not require a ligation step;

hybridizing a second probe having known nucleic acid sequences to at least a portion of the immobilized polynucleotide library fragments;

identifying at least a portion of the second probe hybridized to the immobilized polynucleotide library fragments; and assigning to each hybridized fragment a nucleic acid sequence that is the complement of a plurality of nucleotides of the nucleic acid sequence of the second probe hybridized to the immobilized polynucleotide library fragment, wherein the assigning does not require a ligation step.

2. The method of claim 1 further comprising amplifying the plurality of library polynucleotide fragments.

3. The method of claim 2 wherein amplifying the plurality of library polynucleotide fragments comprises:

providing a plurality of substrates, at least one of the substrates comprising a first end PCR primer and a second end PCR primer affixed to the substrate, wherein providing a polynucleotide library comprising a plurality of polynucleotide fragments comprises:

fragmenting a nucleic acid molecule, thereby producing a plurality of nucleic acid fragments;

ligating a first end PCR primer to a first end of at least one fragment, and a second end PCR primer to a second end of the at least one fragment, wherein the PCR primers comprise a recognition site for a restriction enzyme that cuts remotely from its recognitions site; and digesting the at least one fragment; and amplifying the digested fragment; and wherein ligating the first end PCR primer to the polynucleotide fragment of the library, or ligating the second end PCR primer to the polynucleotide fragment of the library, comprises affixing the library fragment to the substrate via an affixed end PCR primer;

suspending the plurality of substrates in an emulsion wherein at least one emulsion droplet comprises:

one substrate to which one library fragment is affixed; and free PCR components; and amplifying the library fragment.

* * * * *